(12) United States Patent
Pippig et al.

(10) Patent No.: US 6,790,614 B1
(45) Date of Patent: Sep. 14, 2004

(54) SELECTABLE CELL SURFACE MARKER GENES

(75) Inventors: Susanne Dagmar Pippig, San Francisco, CA (US); Gabor Veres, Palo Alto, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/715,249

(22) Filed: Nov. 17, 2000

Related U.S. Application Data

(60) Provisional application No. 60/266,331, filed on Mar. 30, 2000, provisional application No. 60/304,204, filed on Nov. 16, 2000, and provisional application No. 60/166,594, filed on Nov. 19, 1999.

(51) Int. Cl.$^7$ .................. C12Q 1/68; G01N 33/567; G01N 33/574; C12N 9/00; C07K 6/00
(52) U.S. Cl. .................. 435/6; 435/7.21; 435/7.23; 435/7.92; 435/69.1; 435/183; 435/325; 435/332; 435/455; 435/456; 530/387.9; 530/388.26; 536/23.1
(58) Field of Search .................. 435/6, 7.21, 7.23, 435/7.92, 183, 325, 332, 455, 456; 530/387.9, 388.26; 536/23.1

(56) References Cited

U.S. PATENT DOCUMENTS

| | | | |
|---|---|---|---|
| 5,011,912 A | | 4/1991 | Hopp et al. |
| 5,061,620 A | | 10/1991 | Tsukamoto et al. |
| 5,409,813 A | | 4/1995 | Schwartz |
| 5,656,473 A | | 8/1997 | Valenzuela et al. |
| 5,677,136 A | | 10/1997 | Simmons et al. |
| 5,750,397 A | | 5/1998 | Tsukamoto et al. |
| 6,107,477 A | | 8/2000 | Whitney et al. |
| 6,235,729 B1 | * | 5/2001 | Chen et al. |

FOREIGN PATENT DOCUMENTS

| | | | |
|---|---|---|---|
| WO | WO 91/03489 A1 | * | 3/1991 |
| WO | WO 93/05148 | | 8/1993 |
| WO | WO 94/29438 | | 12/1994 |
| WO | WO 95/06723 | | 3/1995 |
| WO | WO 97/21824 | | 6/1997 |
| WO | WO 97/21825 | | 6/1997 |
| WO | WO 98/19540 | | 5/1998 |

OTHER PUBLICATIONS

Verma et al (1997) Nature 389:239–242.*
Palu et al (1999) J. Biotechnol. 68: 1–13.*
Luo et al (2000) Nature Biotechnology 18:33–37.*
Fox, ASM News, Feb. 2000, 66 (2): 1–3.*
Kashles et al (1991) Mol Cell Biol 11:1454–1463.*
Chida et al. Role of Cytokine Signaling Molecules in Erythroid Differentiation of Mouse Fetal Liver Hematopoietic Cells: Functional Analysis of Signaling Molecules by Retrovirus–Mediated Expression. Blood, vol. 93, No. 5(Mar. 1, 1999) pp 1567–1578.*

Bregni, et al, Blood 80:1418–1422; (Sep. 1992).
Apel, et al., Neuron 18:623–635; (Apr. 1997).
Glass, et al., Cell 85:513–523; (May 1996).
Hesser, et al. FEBS Letters 442:133–137 (1999).
Horvathova, et al., Biol. Trace Elem. Res., 69:15–26 (1999).
Humphrey, et al., Biochem. Biophys. Res. Commun., 178:1413–1420 (1991).
Humphrey, et al., Proc. Natl. Acad. Sci. USA, 87:4207–4211 (1990).
Jolly, et al., Proc. Natl. Acad. Sci. USA, 80:477–481 (1983).
Lawrence, et al., Science, 249(4971):928–932 (1990).
Lax, et al., Mol. Cell. Biol., 8:1970–1978 (May 1988).
Lin, et al., Science, 224:843–848 (May 1984).
Livneh, et al., Cell, 40:599–607 (Mar. 1985).
Merlino, et al., Mol. Cell. Biol., 5:1722–1734 (Jul. 1985).
Moscatello, et al., Oncogene, 13:85–96 (1996).
O'Rourke, et al., Oncogene, 16:1197–1207 (1998).
Persons, et al., Blood, 90(5):1777–1786 (Sep. 1997).
Reddy, et al., Mol. Brain Res., 8:137–141 (1990).
Simmen, et al., Biochem. Biophys. Res. Commun., 124:125–132 (Oct. 1984).
Ullrich, et al., Cell, 61:203–212 (Apr. 1990).
Ullrich, et al., Nature, 309:418–425 (May 1984).
Van der Geer, et al., Annu. Rev. Cell Biol., 10:251–337 (1994).
Valenzuela, et al., Neuron, 15(3):573–584 (Sep. 1995).
Xu, et al., Exp. Hemat., 22:223–230 (1994).
Xu, et al., Nature, 309:806–810 (1984).
Yau, et al., Exp. Hematol., 18:219–222 (1990).
Hildinger, et al., "Bicistronic Retroviral Vectors for Combining Myeloprotection with Cell–Surface Marking," *Gene Therapy*, 6:1222–1230 (1999).

* cited by examiner

*Primary Examiner*—Gerry Leffers
*Assistant Examiner*—Maria Marvich
(74) *Attorney, Agent, or Firm*—Peter Herridge

(57) ABSTRACT

The present invention concerns a method of identifying genetically modified mammalian cells using a mutated protein-tyrosine kinase receptor (PTKR) as a selectable marker in mammalian cells. Particularly preferred mutated PTKR selective markers are mutated epidermal growth factor receptor (EGFR) family members, and muscle specific tyrosine kinase receptor (MuSK-R) family members. Further a method for the immunoselection of transduced mammalian cells is disclosed comprising retrovirally transducing mammalian cells with a nucleic acid sequence encoding a mutated EGFR, incubating the transduced cells with a marked antibody which recognizes and binds specifically to the mutated PTKR, and identifying the marked transduced cells.

43 Claims, 8 Drawing Sheets

| | | | | | |
|---|---|---|---|---|---|
| MRPSGTAGAA | LLALLAALCP | ASRALEEKKV | CQGTSNKLTQ | LGTFEDHFLS | 50 |
| LQRMFNNCEV | VLGNLEITYV | QRNYDLSFLK | TIQEVAGYVL | IALNTVERIP | 100 |
| LENLQIIRGN | MYYENSYALA | VLSNYDANKT | GLKELPMRNL | QEILHGAVRF | 150 |
| SNNPALCNVE | SIQWRDIVSS | DFLSNMSMDF | QNHLGSCQKC | DPSCPNGSCW | 200 |
| GAGEENCQKL | TKIICAQQCS | GRCRGKSPSD | CCHNQCAAGC | TGPRESDCLV | 250 |
| CRKFRDEATC | KDTCPPLMLY | NPTTYQMDVN | PEGKYSFGAT | CVKKCPRNYV | 300 |
| VTDHGSCVRA | CGADSYEMEE | DGVRKCKKCE | GPCRKVCNGI | GIGEFKDSLS | 350 |
| INATNIKHFK | NCTSISGDLH | ILPVAFRGDS | FTHTPPLDPQ | ELDILKTVKE | 400 |
| ITGFLLIQAW | PENRTDLHAF | ENLEIIRGRT | KQHGQFSLAV | VSLNITSLGL | 450 |
| RSLKEISDGD | VIISGNKNLC | YANTINWKKL | FGTSGQKTKI | ISNRGENSCK | 500 |
| ATGQVCHALC | SPEGCWGPEP | RDCVSCRNVS | RGRECVDKCN | LLEGEPREFV | 550 |
| ENSECIQCHP | ECLPQAMNIT | CTGRGPDNCI | QCAHYIDGPH | CVKTCPAGVM | 600 |
| GENNTLVWKY | ADAGHVCHLC | HPNCTYGCTG | PGLEGCPTNG | PKIPSIATGM | 650 |
| VGALLLLLVV | ALGIGLFMRR | RHIVRKRTLR | RLLQERELVE | PLTPSGEAPN | 700 |
| QALLRILKET | EFKKIKVLGS | GAFGTVYKGL | WIPEGEKVKI | PVAIKELREA | 750 |
| TSPKANKEIL | DEAYVMASVD | NPHVCRLLGI | CLTSTVQLIT | QLMPFGCLLD | 800 |
| YVREHKDNIG | SQYLLNWCVQ | IAKGMNYLED | RRLVHRDLAA | RNVLVKTPQH | 850 |
| VKITDFGLAK | LLGAEEKEYH | AEGGKVPIKW | MALESILHRI | YTHQSDVWSY | 900 |
| GVTVWELMTF | GSKPYDGIPA | SEISSILEKG | ERLPQPPICT | IDVYMIMVKC | 950 |
| WMIDADSRPK | FRELIIEFSK | MARDPQRYLV | IQGDERMHLP | SPTDSNFYRA | 1000 |
| LMDEEDMDDV | VDADEYLIPQ | QGFFSSPSTS | RTPLLSSLSA | TSNNSTVACI | 1050 |
| DRNGLQSCPI | KEDSFLQRYS | SDPTGALTED | SIDDTFLPVP | EYINQSVPKR | 1100 |
| PAGSVQNPVY | HNQPLNPAPS | RDPHYQDPHS | TAVGNPEYLN | TVQPTCVNST | 1150 |
| FDSPAHWAQK | GSHQISLDNP | DYQQDFFPKE | AKPNGIFKGS | TAENAEYLRV | 1200 |
| APQSSEFIGA | | | | | 1210 |

FIGURE 2

| | | | | | |
|---|---|---|---|---|---|
| ATGCGACCCT | CCGGGACGGC | CGGGGCAGCG | CTCCTGGCGC | TGCTGGCTGC | 50 |
| GCTCTGCCCG | GCGAGTCGGG | CTCTGGAGGA | AAAGAAAGTT | TGCCAAGGCA | 100 |
| CGAGTAACAA | GCTCACGCAG | TTGGGCACTT | TTGAAGATCA | TTTTCTCAGC | 150 |
| CTCCAGAGGA | TGTTCAATAA | CTGTGAGGTG | GTCCTTGGGA | ATTTGGAAAT | 200 |
| TACCTATGTG | CAGAGGAATT | ATGATCTTTC | CTTCTTAAAG | ACCATCCAGG | 250 |
| AGGTGGCTGG | TTATGTCCTC | ATTGCCCTCA | ACACAGTGGA | GCGAATTCCT | 300 |
| TTGGAAAACC | TGCAGATCAT | CAGAGGAAAT | ATGTACTACG | AAAATTCCTA | 350 |
| TGCCTTAGCA | GTCTTATCTA | ACTATGATGC | AAATAAAACC | GGACTGAAGG | 400 |
| AGCTGCCCAT | GAGAAATTTA | CAGGAAATCC | TGCATGGCGC | CGTGCGGTTC | 450 |
| AGCAACAACC | CTGCCCTGTG | CAACGTGGAG | AGCATCCAGT | GGCGGGACAT | 500 |
| AGTCAGCAGT | GACTTTCTCA | GCAACATGTC | GATGGACTTC | CAGAACCACC | 550 |
| TGGGCAGCTG | CCAAAAGTGT | GATCCAAGCT | GTCCCAATGG | GAGCTGCTGG | 600 |
| GGTGCAGGAG | AGGAGAACTG | CCAGAAACTG | ACCAAAATCA | TCTGTGCCCA | 650 |
| GCAGTGCTCC | GGGCGCTGCC | GTGGCAAGTC | CCCCAGTGAC | TGCTGCCACA | 700 |
| ACCAGTGTGC | TGCAGGCTGC | ACAGGCCCCC | GGGAGAGCGA | CTGCCTGGTC | 750 |
| TGCCGCAAAT | TCCGAGACGA | AGCCACGTGC | AAGGACACCT | GCCCCCCACT | 800 |
| CATGCTCTAC | AACCCCACCA | CGTACCAGAT | GGATGTGAAC | CCCGAGGGCA | 850 |
| AATACAGCTT | TGGTGCCACC | TGCGTGAAGA | AGTGTCCCCG | TAATTATGTG | 900 |
| GTGACAGATC | ACGGCTCGTG | CGTCCGAGCC | TGTGGGCCG | ACAGCTATGA | 950 |
| GATGGAGGAA | GACGGCGTCC | GCAAGTGTAA | GAAGTGCGAA | GGGCCTTGCC | 1000 |
| GCAAAGTGTG | TAACGGAATA | GGTATTGGTG | AATTTAAAGA | CTCACTCTCC | 1050 |
| ATAAATGCTA | CGAATATTAA | ACACTTCAAA | AACTGCACCT | CCATCAGTGG | 1100 |
| CGATCTCCAC | ATCCTGCCGG | TGGCATTTAG | GGGTGACTCC | TTCACACATA | 1150 |
| CTCCTCCTCT | GGATCCACAG | GAACTGGATA | TTCTGAAAAC | CGTAAAGGAA | 1200 |
| ATCACAGGGT | TTTTGCTGAT | TCAGGCTTGG | CCTGAAAACA | GGACGGACCT | 1250 |
| CCATGCCTTT | GAGAACCTAG | AAATCATACG | CGGCAGGACC | AAGCAACATG | 1300 |
| GTCAGTTTTC | TCTTGCAGTC | GTCAGCCTGA | ACATAACATC | CTTGGGATTA | 1350 |
| CGCTCCCTCA | AGGAGATAAG | TGATGGAGAT | GTGATAATTT | CAGGAAACAA | 1400 |

FIGURE 3A

| | |
|---|---|
| AAATTTGTGC TATGCAAATA CAATAAACTG GAAAAAACTG TTTGGGACCT | 1450 |
| CCGGTCAGAA AACCAAAATT ATAAGCAACA GAGGTGAAAA CAGCTGCAAG | 1500 |
| GCCACAGGCC AGGTCTGCCA TGCCTTGTGC TCCCCCGAGG GCTGCTGGGG | 1550 |
| CCCGGAGCCC AGGGACTGCG TCTCTTGCCG GAATGTCAGC CGAGGCAGGG | 1600 |
| AATGCGTGGA CAAGTGCAAG CTTCTGGAGG GTGAGCCAAG GGAGTTTGTG | 1650 |
| GAGAACTCTG AGTGCATACA GTGCCACCCA GAGTGCCTGC CTCAGGCCAT | 1700 |
| GAACATCACC TGCACAGGAC GGGGACCAGA CAACTGTATC CAGTGTGCCC | 1750 |
| ACTACATTGA CGGCCCCCAC TGCGTCAAGA CCTGCCCGGC AGGAGTCATG | 1800 |
| GGAGAAAACA ACACCCTGGT CTGGAAGTAC GCAGACGCCG GCCATGTGTG | 1850 |
| CCACCTGTGC CATCCAAACT GCACCTACGG ATGCACTGGG CCAGGTCTTG | 1900 |
| AAGGCTGTCC AACGAATGGG CCTAAGATCC CGTCCATCGC CACTGGGATG | 1950 |
| GTGGGGGCCC TCCTCTTGCT GCTGGTGGTG GCCCTGGGGA TCGGCCTCTT | 2000 |
| CATGCGAAGG CGCCACATCG TTCGGAAGCG CACGCTGCGG AGGCTGCTGC | 2050 |
| AGGAGAGGGA GCTTGTGGAG CCTCTTACAC CAGTGGAGA AGCTCCCAAC | 2100 |
| CAAGCTCTCT TGAGGATCTT GAAGGAAACT GAATTCAAAA AGATCAAAGT | 2150 |
| GCTGGGCTCC GGTGCGTTCG GCACGGTGTA TAAGGGACTC TGGATCCCAG | 2200 |
| AAGGTGAGAA AGTTAAAATT CCCGTCGCTA TCAAGGAATT AAGAGAAGCA | 2250 |
| ACATCTCCGA AAGCCAACAA GGAAATCCTC GATGAAGCCT ACGTGATGGC | 2300 |
| CAGCGTGGAC AACCCCCACG TGTGCCGCCT GCTGGGCATC TGCCTCACCT | 2350 |
| CCACCGTGCA ACTCATCACG CAGCTCATGC CCTTCGGCTG CCTCCTGGAC | 2400 |
| TATGTCCGGG AACACAAAGA CAATATTGGC TCCCAGTACC TGCTCAACTG | 2450 |
| GTGTGTGCAG ATCGCAAAGG GCATGAACTA CTTGGAGGAC CGTCGCTTGG | 2500 |
| TGCACCGCGA CCTGGCAGCC AGGAACGTAC TGGTGAAAAC ACCGCAGCAT | 2550 |
| GTCAAGATCA CAGATTTTGG GCTGGCCAAA CTGCTGGGTG CGGAAGAGAA | 2600 |
| AGAATACCAT GCAGAAGGAG GCAAAGTGCC TATCAAGTGG ATGGCATTGG | 2650 |
| AATCAATTTT ACACAGAATC TATACCCACC AGAGTGATGT CTGGAGCTAC | 2700 |
| GGGGTGACCG TTTGGGAGTT GATGACCTTT GGATCCAAGC CATATGACGG | 2750 |
| AATCCCTGCC AGCGAGATCT CCTCCATCCT GGAGAAAGGA GAACGCCTCC | 2800 |

FIGURE 3B

| | | | | |
|---|---|---|---|---|
| CTCAGCCACC | CATATGTACC | ATCGATGTCT | ACATGATCAT | GGTCAAGTGC | 2850
| TGGATGATAG | ACGCAGATAG | TCGCCCAAAG | TTCCGTGAGT | TGATCATCGA | 2900
| ATTCTCCAAA | ATGGCCCGAG | ACCCCAGCG | CTACCTTGTC | ATTCAGGGGG | 2950
| ATGAAAGAAT | GCATTTGCCA | AGTCCTACAG | ACTCCAACTT | CTACCGTGCC | 3000
| CTGATGGATG | AAGAAGACAT | GGACGACGTG | GTGGATGCCG | ACGAGTACCT | 3050
| CATCCCACAG | CAGGGCTTCT | TCAGCAGCCC | CTCCACGTCA | CGGACTCCCC | 3100
| TCCTGAGCTC | TCTGAGTGCA | ACCAGCAACA | ATTCCACCGT | GGCTTGCATT | 3150
| GATAGAAATG | GGCTGCAAAG | CTGTCCCATC | AAGGAAGACA | GCTTCTTGCA | 3200
| GCGATACAGC | TCAGACCCCA | CAGGCGCCTT | GACTGAGGAC | AGCATAGACG | 3250
| ACACCTTCCT | CCCAGTGCCT | GAATACATAA | ACCAGTCCGT | TCCCAAAAGG | 3300
| CCCGCTGGCT | CTGTGCAGAA | TCCTGTCTAT | CACAATCAGC | CTCTGAACCC | 3350
| CGCGCCCAGC | AGAGACCCAC | ACTACCAGGA | CCCCACAGC | ACTGCAGTGG | 3400
| GCAACCCCGA | GTATCTCAAC | ACTGTCCAGC | CCACCTGTGT | CAACAGCACA | 3450
| TTCGACAGCC | CTGCCCACTG | GGCCCAGAAA | GGCAGCCACC | AAATTAGCCT | 3500
| GGACAACCCT | GACTACCAGC | AGGACTTCTT | TCCCAAGGAA | GCCAAGCCAA | 3550
| ATGGCATCTT | TAAGGGCTCC | ACAGCTGAAA | ATGCAGAATA | CCTAAGGGTC | 3600
| GCGCCACAAA | GCAGTGAATT | TATTGGAGCA | TGA | | 3630

FIGURE 3C

First PCR Reaction
EGFR1 + EGFR3    primer
a.) 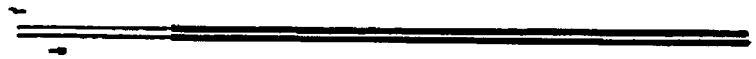 EGFR cDNA
PCR product a
encoding aa 1 to 24 fused to aa 313 to 319
EGFR2    +    EGFR2220R   primer
b.)  EGFR cDNA
PCR product b
encoding aa 18 to 24 fused to aa 313 to 678
Second PCR Reaction
a.) 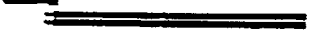
PCR product a + b
overlap extension
PCR product c
encoding aa 1 to 24 fused to aa 313 to 678
with a stop codon in position 679
EGFR1    +    EGFR2220R   primer
b.) 
amplification of
PCR product c
FIGURE 4

| | | | | | |
|---|---|---|---|---|---|
| MRELVNIPLV | HILTLVAFSG | TEKLPKAPVI | TTPLETVDAL | VEEVATFMCA | 50 |
| VESYPQPEIS | WTRNKILIKL | PDTRYSIREN | GQLLTILSVE | DSDDGIYCCT | 100 |
| ANNGVGGAVE | SCGALQVKMK | PKITRPPINV | KIIEGLKAVL | PCTTMGNPKP | 150 |
| SVSWIKGDSP | LRENSRIAVL | ESGSLRIHNV | QKEDAGQYRC | VAKNSLGTAY | 200 |
| SKVVKLEFEV | FARILRAPES | HNVTFGSFVT | LHCTATGIPV | PTITWIENGN | 250 |
| AVSSGSIQES | VKDRVIDSRL | QLFITKPGLY | TCIATNKHGE | KPSTAKAAAT | 300 |
| ISIAEWSKPQ | KDNKGYCAQY | RGEVCNAVLA | KDALVFLNTS | YADPEEAQEL | 350 |
| LVHTAWNELK | VVSPVCRPAA | EALLCNHIFQ | ECSPGVVPTP | IPICREYCLA | 400 |
| VKELFCAKEW | LVMEEKTHRG | LYRSEMHLLS | VPKCSKLPSM | HWDPTACARL | 450 |
| PHLDYNKENL | KTFPPMTSSK | PSVDIPNLPS | SSSSSFSVSP | TYSMTVIISI | 500 |
| MSSFAIFVLL | TITTLYCCRR | RKQWKNKKRE | SAAVTLTTLP | SELLLDRLHP | 550 |
| NPMYQRMPLL | LNPKLLSLEY | PRNNIEYVRD | IGEGAFGRVF | QARAPGLLPY | 600 |
| EPFTMVAVKM | LKEEASADMQ | ADFQREAALM | AEFDNPNIVK | LLGVCAVGKP | 650 |
| MCLLFEYMAY | GDLNEFLRSM | SPHTVCSLSH | SDLSMRAQVS | SPGPPPLSCA | 700 |
| EQLCIARQVA | AGMAYLSERK | FVHRDLATRN | CLVGENMVVK | IADFGLSRNI | 750 |
| YSADYYKANE | NDAIPIRWMP | PESIFYNRYT | TESDVWAYGV | VLWEIFSYGL | 800 |
| QPYYGMAHEE | VIYYVRDGNI | LSCPENCPVE | LYNLMRLCWS | KLPADRPSFT | 850 |
| SIHRILERMC | ERAEGTVSV | | | | 869 |

FIGURE 6

SELECTABLE CELL SURFACE MARKER GENES

This application claims the benefit under 35 USC §119(e) of the following United States provisional patent applications: (1) Provisional Application No. 60/166,594, filed Nov. 19, 1999, for "Selectable Cell Surface Marker Genes;" (2) Provisional Application No. 60/304,204, filed Nov. 19, 1999, as application Ser. No. 09/444,038 for "Selective Marker Genes," and subject to a Petition for Conversion to Provisional Application, filed Nov. 16, 2000; and (3) Provisional Application No. 60/266,331, filed Mar. 30, 2000 as application Ser. No. 09/539,248 for "Selectable Marker Genes," and subject to a Petition for Conversion to Provisional Application, filed Nov. 16, 2000. The disclosures of these three provisional applications are incorporated herein by reference in their entirety.

This invention relates to a method of identifying genetically modified cells using a mutated protein-tyrosine kinase receptor (PTKR), particularly a mutated epidermal growth factor receptor (EGFR) family member or a mutated muscle specific kinase (MuSK) family member as a selectable cell marker.

BACKGROUND OF THE INVENTION

The use of selectable markers is well known for the identification of prokaryotic and eukaryotic cells, and the use is essential because frequently when a DNA sequence of interest is introduced into a cell it will not necessarily lead to a phenotype that is readily determined. The number of selectable markers used in identifying eukaryotic cells and especially mammalian cells has been limited. In the past, selectable markers that conferred drug resistance were employed (i.e. G-418 and hygromycin). More recently, selectable markers that are combined with fluorescence activated cell sorting (FACS) have been used, for example, green fluorescent protein (GFP). Alternatively, antibodies that recognize a cell surface molecule may be coupled to a fluorophore to help identify the cells of interest.

Several cell surface molecules have been used as a selectable cell marker including murine CD8, CD24, and human Low-Affinity Nerve Growth Factor Receptor (NGFR). Reference is made to the following publications; WO95/06723; WO98/19540; Jolly, et al., Proc. Natl. Acad. Sci. 80: 477 (1983); and Reddy, et al., Mol. Brain Res. 8:137 (1990). Some of these cell surface molecules have been mutated in their intracellular domain to avoid signaling of the molecule when binding to their ligand. However upon ligand binding some of the intracellularly mutated molecules may homo-, heterodimerize or trimerize. If a newly introduced molecule in the cell should heterodimerize with endogenous receptors a dominant negative effect may result. The present invention provides cell surface markers that do not heterodimerize with endogenous receptors.

SUMMARY OF THE INVENTION

The present invention provides a method of identifying genetically modified mammalian cells comprising introducing a nucleic acid sequence encoding a mutated protein-tyrosine kinase receptor (PTKR) operatively linked to an expression control sequence into a cell to form a genetically modified cell; allowing expression of the mutated PTKR in the genetically modified cell; and identifying said genetically modified cell expressing the mutated PTKR. In a preferred embodiment the mutated PTKR is a mutated epidermal growth factor receptor (EGFR) family member (or MuSK family member), particularly preferred is a mutated EGFR1 and more specifically the sequences given the designation EGFR1-I and EGFR1-II. In a second embodiment the introducing step is accomplished by incorporating the nucleic acid sequence encoding the mutated PTKR, and particularly the mutated EGFR into a vector and introducing the vector into a cell. The preferred vectors are retroviral vectors. In a further embodiment the mammalian cells are human cells, particularly hematopoietic cells, liver cells, endothelial vascular cells, and smooth muscle cells, more particularly hematopoietic cells. In yet another embodiment a beterologous gene is incorporated into the construct or vector comprising the mutated PTKR marker sequence. In yet a further embodiment the identifying step is accomplished by contacting the genetically modified cells with an antibody that recognizes and binds to the mutated PTKR. In yet another embodiment the identifying step separates the genetically modified cells from the non-genetically modified cells.

In a second aspect, the invention provides a method of identifying genetically modified mammalian cells comprising the steps of incorporating into a vector a nucleic acid sequence encoding a mutated epidermal growth factor receptor (EGFR) family member operatively linked to an expression control sequence; introducing the vector into a mammalian cell to form a genetically modified cell; allowing expression of the mutated EGFR in the genetically modified cell; and identifying said genetically modified cell expressing the mutated EGFR. In a preferred embodiment the mutated EGFR is EGFR1-I or EGFR1-II and the vector is a retroviral vector.

In a third aspect, the invention is directed to a method for the immunoselection of transduced mammalian cells comprising, retrovirally transducing mammalian cells with a nucleic acid sequence encoding a mutated epidermal growth factor receptor (EGFR) family member operatively linked to an expression control sequence; incubating the transduced cells with a marked antibody that recognizes and binds specifically to the mutated EGFR; and identifying the marked transduced cells. In a preferred embodiment the cells are human cells, particularly hematopoietic cells. In another embodiment the cells are transduced by a retroviral vector derived from the group consisting of moloney murine leukemia virus (MoMLV), myeloproliferative sarcoma virus (MPSV), murine embryonic stem cell virus (MESV), murine stem cell virus (MSCV) and spleen focus forming virus (SFFV). In a further embodiment the cells are transduced with a vector derived from a lentivirus. In yet a further embodiment the method includes the step of separating the identified marked transduced cells from non-marked cells. In yet another embodiment the method includes the step of expanding the marked transduced cells.

In a fourth aspect, the invention is directed to a method of identifying mammalian cells expressing a protein of interest, comprising the steps of, introducing into a mammalian cell a nucleic acid sequence encoding a mutated PTKR operatively linked to an expression control sequence and a nucleic acid sequence encoding a protein of interest; culturing the resulting mammalian cells; and identifying cells which express the mutated PTKR thereby obtaining cells which express the protein of interest.

BRIEF DESCRIPTION OF THE DRAWINGS

FIG. 2 illustrates the amino acid sequence of a wild-type (WT) EGFR1 and corresponds to SEQ ID NO: 2. The signal sequence is represented as amino acid residue 1 to 24. The extracellular domain includes amino acid residues 25 through 645, the transmembrane domain includes amino acid residues 646 through 668, and the cytoplasmic domain includes amino acid residues 669 through 1210. The tyrosine kinase domain is located at amino acid residues 718 though 964, and the threonine phosphorylation site is located at amino acid residue 678.

FIG. 3 illustrates the nucleotide sequence of the wild-type (WT) EGFR1 encoding the amino acid sequence of FIG. 2 and corresponds to SEQ ID NO: 1.

FIG. 4 illustrates the general scheme used to generate a deletion in the extracellular domain and intracellular domain of the EGFR sequence depicted in FIGS. 2 and 3.

FIG. 6 illustrates a MuSK-R designated hMuSK-R and corresponds to the nucleic acid sequence as set forth in SEQ ID NO:7 and the amino acid sequence as set forth in SEQ ID NO:8.

DETAILED DESCRIPTION OF THE INVENTION

Figure 1:
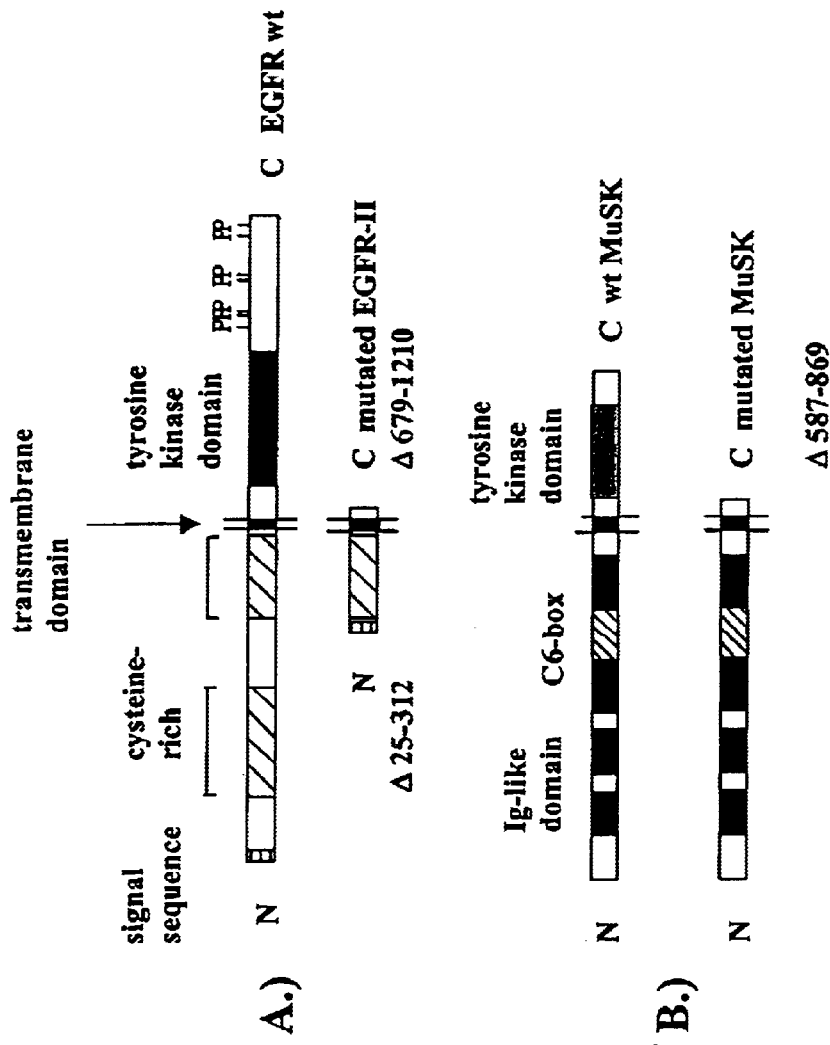
FIG. 1A is a schematic representation of a wild-type (WT) EGFR molecule and the mutated EGFR1-II with amino acid residues deleted from both the cytoplasmic and extracellular domains.
FIG. 1B illustrates the wild-type and the mutated MuSK. Both EGFR-II and the mutated MuSK can be used as selectable cell surface markers.

The practice of the present invention will employ, unless otherwise indicated conventional techniques of cell biology, molecular biology, cell culture, immunology, virology, and the like which are in the skill of one in the art. These techniques are filly disclosed in the current literature and reference is made specifically to Sambrook, Fritsch and Maniatis eds., "Molecular Cloning, A Laboratory Manual", 2$^{nd}$ Ed., Cold Springs Harbor Laboratory Press, (1989); Celis, J. E. "Cell Biology, A Laboratory Handbook", Academic Press, Inc. (1994); Coligan et al., "Current Protocols in Immunology", John Wiley and Sons (1991); and Harlow et al., "Antibodies: A Laboratory Manual" (1988), Biosupplynet Source Book (1999), Cold Springs Harbor Laboratory.

All publications and patent applications cited in this specification are indicative of the level of skill of those skilled in the art to which this invention pertains, and are hereby incorporated by reference in their entirety.

As used in this specification and the claims, the singular form "a", "an" and "the" include plural references unless the context clearly dictates otherwise. For example, a stem cell includes a plurality of stem cells.

The selectable marker of the instant invention is a mutated protein-tyrosine kinase receptor (PTKR) molecule. PTKR molecules are activated by polypeptide ligands, and are closely related in their catalytic domains. They are Type I transmembrane proteins, with their N-termini outside the cell and single membrane-spanning regions. (See van der Geero et al., Annu. Rev. Cell Biol. 10:251 (1994)). As used herein PTKRs include but are not limited to the following subfamilies, MuSK-R which is believed to initiate the formation of neuromuscular junctions in response to agrin (Glass, et al. *Cell* 85:513 (1996), epidermal growth factor receptor (EGFR), platelet-derived growth factor receptor (PDGFR), insulin receptor (INSR), nerve growth factor receptor (NGFR), fibroblast growth factor receptor (FGFR), and EPH. Each subfamily is comprised of various members. The PDGFR family includes PDGF receptor α, PDGF receptor β, SCF receptor (c-Kit), CSF-1 receptor (c-Fms), Flk2 (Flt3), FLT1 (Quek1), Flk1 (KDR), and FLT4 (Quk2). The INSF subfamily includes insulin receptor, IGF-1 receptor, IRR, ROS and Ltk. The NGFR subfamily includes NGFR receptor (TrkA), TrkB, and TrkC. The EGFR family includes EGFR1, EGFR2, EGFR3, and EGFR4. One skilled in the art is aware of alternative nomenclature for these members e.g. EGFR1 has been referred to as EGFR, HER, c-ErbB, and ErbB-1; EGFR2 has been referred to as HER2, Neu and ErbB-2; EGFR3 has been referred to as HER3 and ErbB-3; and EGFR4 has been referred to as HER4 and ErbB4. (Ullrich and Schlessinger, Cell, 61: 203–212 (1990)).

The mutated PTKRs of the present invention include a modification in a PTKR molecule so that the receptor no longer possesses the signaling activity of the corresponding unmodified (wild type) receptor. For the purpose of the present disclosure, "Wild-Type PTKRs" include not only naturally occurring PTKRs but also may include genetically engineered PTKRs molecules wherein the PTKR molecule has undergone changes in the DNA sequence that do not significantly effect the properties of the protein tyrosine kinase receptor molecule. These changes include ones that do not change the encoded amino acid sequence, ones that result in conservative substitutions of amino acid sequences, or ones that result in one or a few amino acid deletions or additions. Suitable substitutions are known by those skilled in the art. Amino acid residues which can be conservatively substituted for one another include, but are not limited to, glycine/alanine; valine/isoleucine/leucine, asparagine/glutamine; aspartic acid/glutamic acid; serine/threonine; lysine/arginine; and phenylalanine/tyrosine.

A modification of the wild-type PTKR molecule may include deletions, truncations and the like. More specifically, mutated PTKRs of the invention include a modification, however, obtained, in the cytoplasmic domain causing the molecule to be devoid of signaling activity. Signaling activity may be generally defined as activity that triggers a response pathway in the cytosol to the nucleus that ultimately leads to activation of transcription. The mutated PTKRs according to the invention may include a modification in the extracellular domain. However, preferably the extracellular domain should still be capable of binding an antibody. In general, the smallest peptide fragment of the extracellular domain capable of binding an antibody would be approximately 15 amino acid residues, more preferably at least 50 amino acid residues.

In a preferred embodiment, the selective marker PTKR is a mutated member of the EGFR family. The members of the EGFR family have similar overall topology and significant relatedness in amino acid sequence. Members of this family are not limited to the above-enumerated members, but include new members sharing common features, such as a single transmembrane domain; two cysteine rich regions of approximately 100 to 200 amino acid residues, and a single tyrosine kinase domain. Further, members of the EGFR family can beterodimerize with other members of the EGFR family.

A preferred mutated EGFR family member is EGFR1. EGFR1 is a high affinity receptor for a number of ligands including but not limited to epidermal growth factor (EGF), transforming growth factor α (TGFα) and amphiregulin. Various EGFR sequences have been identified and reference is made to EMBL/GenBank Accession Numbers: X00588/ X06370 (Ullrich, et al., Nature 309:418 (1984)); K01885/ K02047, (Lin et al., Science 224:843 (1984)); K03193 (Merlino, et al., Mol. Cell. Biol 5:1722 (1985)): X00663 (Xu, et al., Nature 309:806 (1984); AC006977; M38425 (Simmen, et al., Biochem. Biophys. Res. Commun. 124:125 (1984)); and M20386 (Lax, et al., Mol. Cell. Biol. 8:1970 (1988)). Several EGFRs have been identified in invertebrate species, for example Drosophila having EMBL/GenBank Accession Number K03054 (Livneh, et al., Cell 40:599 (1985)).

The domain structure of wild-type EGFR is schematically illustrated in FIG. 1. EGFR is comprised of a signal peptide that targets the protein to the secretory pathway. The extracellular domain follows the signal sequence. This domain is made up of several hundred amino acids. The extracellular domain means the part of the receptor that normally projects from the cell into the extracellular environment and in the EGFR it contains distinctive Cys residues. The transmembrane domain is generally localized in the cell membrane and consists of a stretch of hydrophobic residues followed by several basic residues. The cytoplasmic domain (also referred to as the intracellular domain) includes the catalytic part of the molecule and is positioned within the cell. This domain contains the substrate binding site and regulatory tyrosine and threonine phosphorylation sites.

Modifications of EGFR family members are known, and particularly mutations of EGFR1 are known. WO 93/05148 discloses three mutations of EGFR1. One mutation (referred to as HER721A) is a point mutation in the cytoplasmic domain of EGFR1 at amino acid position 721. The lysine is changed to alanine. A second mutation (referred to as HERCD-533) involves the C-terminal end of the molecule wherein the intracellular domain was deleted but the transmembrane domain was not. A third mutation (referred to as HERCD-566) includes the C-terminal deletion of 566 amino acids, both the intracellular and transmembrane domains were deleted. Three truncated forms of EGFR have been detected in some rnalignancies: Type I (EGFRvIII) has a large deletion of the extracellular domain (amino acids 6–273) and does not bind EGF (Moscatello, D. K. et al., Oncogene 13:85 (1996)). Type II contains an in-frame deletion of 83 amino acids (520–603) in extracellular domain IV that does not prevent EGF and TGFα binding (Humphrey, P. A. et al., Biophys. Res. Commun. 178:1413 (1991)). Type HIII has an in-frame deletion of 267 amino acids (29–296) in extracellular domains II and III. These two mutations prevent ligand binding (Humphrey, P. A. et al., Proc. Natl. Acad. Sci. USA 87:4207 (1990)).

While specific modifications such as, but not limited to those enumerated above may be known for the EGFR members, the use of a mutated EGFR family member as a selectable marker in mammalian cells is not known. According to the invention preferred modifications to the PTKR molecules and particularly to EGFR molecules include modifications to the cytoplasmic domain, such as deletions of at least 150, preferably at least 250, more preferably at least 400, and still more preferably at least 500 amino acids of the cytoplasmic domain. In a preferred embodiment, the deletions will consist of a truncation of the molecule. Truncations may include deletion of tyrosine phosphorylation sites in the range of 1 to 15 sites and deletion of the kitase catalytic site. However, a mutated EGFR useful as selectable marker in the invention may include more than 1 and fewer than 15 deletions of tyrosine phosphorylation sites. Additionally, the above modifications may include in-frame deletions, such as deletions of at least 50 amino acids of the cytoplasmic domain. These deletions may include deletion of the protein tyrosine-kinase activity. Particularly preferred selectable marker sequences are mutated EGFR1, EGFR2 and EGFR3 molecules wherein at least 400 and preferably 500 amino acids of the cytoplasmic domain are deleted from the corresponding wild-type molecule.

In the present invention, a preferred mutated EGFR molecule is a mutated EGFR1. Particularly preferred is a modified sequence derived from EGFR1 as illustrated in FIGS. 2 and 3 (SEQ ID Nos. 1 and 2). In this EGFR1 molecule, the extracellular domain is encoded by nucleotides 1 through 1935, the transmembrane domain is encoded by nucleotides 1938 through 2004, and the intracellular domain is coded by nucleotides 2007 to 3630. One non-limiting example of a preferred mutated EGFR1 marker is designated EGFR1-I wherein amino acid sequence 679 to 1210 of the cytoplasmic domain as illustrated in FIG. 2 is deleted.

In a second preferred embodiment, the selective marker PTKR is a mutated member of the MuSK-R family. MuSK-R is comprised of a signal sequence or leader sequence that targets the protein to the secretory pathway. The extracellular domain follows the signal sequence. This domain is made up of several hundred amino acids, and while the exact number of amino acid residues varies, typically the extracellular domain includes around 500 amino acids. The extracellular domain is the part of the receptor that normally projects from the cell into the extracellular environment and includes a ligand binding region. The extracellular domain is one of the most distinctive features of the kinase receptors. In MuSK-R, the extracellular domain contains immunoglobulin-like (Ig-like) regions. Typically four Ig-like regions are found. However there are reports of MuSK-Rs with three Ig-like regions. The extracellular domain may include 6 contiguous cysteine residues known as a C6-box. While the location of the C6-box may vary depending on the particular MuSK-R, in certain MuSK-Rs it is found approximately at amino acid residues 373–382. The transmembrane domain is generally localized in the cell membrane and consists of a stretch of hydrophobic residues followed by several basic residues. The intracellular domain (used interchangeably with the cytoplasmic domain) includes the catalytic part of the molecule and is positioned within the cell.

MuSK-Rs are also known in the art as denervated muscle kinase receptors and have been referred to as DmKs (see U.S. Pat. No. 5,656,473 and particularly SEQ ID NOS: 16 and 17 therein). MuSK-R sequences have been isolated and identified from humans, rats, mice, and xenopus. Closely related to human MuSK-R is a receptor isolated from the electric ray *Torpedo californica* designated Torpedo tyrosine kinase receptor, and ROR tyrosine kinase receptors (Jennings, et al. *Proc. Natl. Acad. Sci.* USA 90:2895 (1993); Masiakowski et al., *J Biol. Chem.* 267: 26181–26190 (1992); Valenzuela et al., *Neuron*, 15:573–584 (1995); and Hesser et al., *FEBS Letters*, 442:133–137 (1999)).

Other non-limiting examples of MuSK-Rs available from public depositories such as GeneBank and ATCC include accession numbers: NM005592; AF006464; A448972; AI800924; AI700028; AI341265; AI341122; AI302067; U34985; AA448972; and ATCC 75498. As mentioned above MuSK-R is specific to the skeletal muscle lineage.

The term MuSK-R as used in the present specification and claims is broadly defined to include the known MuSK-Rs (including DmK receptors), isoforms or variants of known MuSK-Rs having similar structure, tyrosine kinase receptors that are functionally similar to known MuSK-Rs and novel MuSK-Rs not previously described that are identified using screening techniques well known to those in the art. Such techniques may include the use of degenerate oligodeoxyribonucleotide primers.

Accordingly, the term MuSK-R when referring to a nucleic acid molecule includes (a) nucleic acid sequences comprising a coding region of a known mammalian MuSK-R; (b) a nucleic acid sequence which hybridizes under stringent conditions to the nucleic acid of (a) and which encodes a mammalian MuSK-R; and (c) a degenerate MuSK-R wherein the MuSK-R has undergone changes in its nucleic acid sequence that does not significantly effect the properties of the MuSK-R protein encoded by the polynucleotide. These changes include ones that do not change the encoded amino acid sequence, ones that result in conservative substitutions of amino acid sequences, or ones that result in one or a few amino acid deletions or additions. Suitable substitutions are known by those skilled in the art. Amino acid residues that can be conservatively substituted for one another include but are not limited to, glycine/alanine; valine/isoleucine/leucine, asparagine/glutamine; asparatic acid/glutamic acid; serine/threonine; lysine/arginine; and phenylalanine/tyrosine. Any conservative amino acid substitution not significantly affecting the properties of a MuSK-R is encompassed by the term. MuSK-R includes not only naturally occurring MuSK-Rs but also may include genetically engineered MuSK-Rs.

The term MuSK-R when referring to a polypeptide encompasses known MuSK receptors, isoforms or variants of MuSK-Rs, and functionally equivalent receptors. A functionally equivalent receptor is a MuSK-R that can compete with a known MuSK-R for binding. More specifically, a functionally equivalent MuSK-R has at least 40%, preferably at least 60%, and more preferably at least 80% identical amino acids to the sequence set forth in SEQ ID NO: 8 and can compete with the MuSK-R illustrated in FIG. 6 for ligand or substrate binding.

According to the invention mutated MuSK-R are used as selective markers to identify genetically modified cells. The marker is introduced on a nucleic acid construct into a target cell that normally does not express a MuSK-R. The term "introduced" is broadly used herein to include inserted, incorporated and the like. When the mutated MuSK-Rs are used as selectable markers the molecule no longer possesses signaling activity. Signaling activity has be generally defined as triggering a response pathway in the cytosol to the nucleus which ultimately leads to activation of transcription. The lack of signaling activity may be due to a) use of a MuSK-R in tissue or cells other than muscle (Glass et al., Cell 85:513–523 (1996)) or b) use of a mutated MuSK-R.

While modifications of MuSK-R may be known, the method of identifying genetically modified cells comprising using a mutated MuSK-R as a selectable marker is not known.

As stated above, the localization of MuSK-R is in muscle tissue and MuSK-R serves as the functional agrin receptor. Agrin is a factor that can induce molecular reorganizations at the motor endplate. Therefore, MuSK-R may be used as a selective marker in tissue other than muscle.

In a preferred embodiment, the modifications to a MuSK-R include truncations and/or deletions of MuSK-Rs. The mutation may occur in the extracellular domain and/or the intracellular domain by means well known in the art. The mutation causes the molecule to be devoid of signaling activity. Preferably the extracellular domain should still be capable of binding an antibody. In general the smallest peptide fragment of the extracellular domain capable of binding an antibody would be approximately 15 amino acid residues, more preferably at least 50 amino acid residues.

A preferred MuSK-R according to the invention is the sequence set forth in SEQ ID NOs: 7 and 8, designated herein as hMuSK-R. The extracellular domain is encoded by nucleotides 1 through 1479, the transmembrane domain is encoded by nucleotides 1480 through 1545, and the intracellular domain is encoded by nucleotides 1546 through 2607. Other preferred MuSK-Rs are molecules closely related to the sequences set forth in SEQ ID NO: 8 and 7. Examples of closely related sequences are the sequences set forth in U.S. Pat No. 5,656,473 particularly NO: 16 and 17 disclosed therein.

Mutants of MuSK-R are known and reference is made to Apel et al., Neuron 18:623–635 (1997). In the present invention, preferred modifications to a MuSK-R include modifications to the cytoplasmic domain such as deletions of at least 150, preferably at least 200, more preferably at least 250, more preferably 300, and most preferably at least 350 amino acids of the cytoplasmic domain. The deletions are preferably truncations. Deletions or truncations may include deletion of tyrosine phosphorylation sites in the range of 1 to 19, preferably 2–15, more preferably 2–10 sites. Additionally the kinase catalytic site may be deleted from a MuSK-R. In one aspect, the kinase catalytic site is found at approximately amino acid residues 672 to 691 of SEQ ID NO: 8. As long as the protein is stably expressed, there is no limitation to the number of sequences deleted or truncated in the cytoplasmic domain.

Particularly preferred mutated MuSK-Rs useful as selectable markers according to the invention include modifications to the MUSK-R sequence set forth in FIG. 6 (SEQ ID NO: 8). In one embodiment the MuSK-R is truncated by least 300 amino acid residues in the cytoplasmic domain. One preferred embodiment includes the deletion of amino acid sequence 538–869 and is designated mMuSK-RI. Another preferred embodiment includes the deletion of amino acid sequence 577–869 and is designated mMuSK-RII.

In addition to modification of the cytoplasmic domain mutations may be made in the extracellular domain. The extracellular domain modification may include deletion of at least about 100 amino acids, preferably at least about 150 amino acids, more preferably at least about 200 amino acids, and still more preferably at least about 250 amino acids. A mutated MuSK-R used as a selectable marker according to the invention preferably should contain an antibody-binding site in the extracellular domain.

In another preferred embodiment, a mutated PTKR, particularly a mutated EGFR or mutated MusSK-R useful as a selectable marker includes both modification of the cytoplasmic domain such as described above, and modification to the extracellular domain. This is expected toto avoid heterodimerization of the mutated PTKR with endogenous receptors.

The extracellular domain modifications may include deletion of at least about 100 amino acids, preferably at least about 150 amino acids, more preferably at least about 200 amino acids, and still more preferably at least about 250 amino acids. In one embodiment, the modification will include removal of one cysteine-rich area generally characterized by an area of about 100 amino acids. Particularly preferred marker sequences are mutated EGFR1, EGFR2 and EGFR3 molecules having not only a truncation in the cytoplasmic domain but also a deletion of at least 200 and preferably at least 250 amino acids of the extracellular domain. As mentioned above, a mutated PTKR as a selectable marker useful in the methods of the invention should preferably include an antibody-binding site in the extracellular domain.

More particularly, a preferred mutated EGFR molecule wherein both the extracellular domain and the cytoplasmic domain are modified is a sequence derived from WT EGFR1 illustrated in FIG. 2 (SEQ ID Nos. 1 and 2). Particularly preferred is a mutated EGFR1 sequence designated EGFR1-II wherein amino acid sequence 25 through 313 of the extracellular domain and amino acid sequence 679 through 1210 of the cytoplasmic domain of FIG. 2 (SEQ ID NO. 2) are deleted.

As used herein a "mutated PTKR" or a "mutated EGFR" or a "mutated MuSK-R" selectable marker refers to nucleotides or protein as appropriate from context. Polynucleotides of the invention may be in the form of RNA or in the form of DNA, which DNA includes cDNA, genomic DNA or synthetic DNA.

General strategies for creating mutations in nucleic acids and proteins are well known. These methods may be used to create mutant PTKRs, particularly mutant EGFR family members useful as selectable markers in the present invention. One skilled in the art is aware that PTKR molecules including members of the EGFR family may be obtained from sources such as various sequence databases including GenBank. Both random and site-directed mutagenesis methods may be effective to create mutations in wild type PTKRs. Random methods encompass altering the sequences within restriction endonuclease sites, inserting an oligonucleotide linker into a plasmid, using chemicals to damage plasmid DNA, and incorporating incorrect nucleotides during in vitro DNA synthesis. However, site-directed mutagenesis may be a more beneficial tool. Particularly preferred site-directed methods include oligonucleotide-directed mutagenesis and polymerase chain reaction (PCR)-amnplified oligonucleotide-directed mutagenesis. These methods are also well known in the art and reference is made to Wu, et al., eds. Methods in Enzymology, Vol. 154: Recombinant DNA, Part E, Academic, NY (1987); Landt, et al., Gene, 96:125–128 (1990); Kirchhoff et al., Methods Mol. Biol. 57:323–333 (1995); Herlitze, et al., Gene 91:143–147 (1990); Sambrook, et al. Molecular Cloning, A Laboratory Manual, supra, and Current Protocols in Molecular Biology, Greene Publishing Associates, John Wiley & Sons, Inc Canada (1988).

The usefulness of a mutated PTKR as a selectable marker concerns the ability to identify genetically modified mammalian cells in vitro, ex vivo, and in vivo. While the mutated PTKR sequence may be introduced into a target cell as part of a nucleic acid construct operatively linked to an expression control sequence, in a preferred embodiment the construct including the mutated PTKR sequence is placed in a vector and then introduced into a target cell. As used herein "operatively linked" refers to an arrangement of elements wherein the components are configured so as to perform their usual function. The control elements need not be contiguous with the coding sequence.

Vectors containing both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). Examples of vectors include vectors derived from viruses, such as baculovirus, retroviruses, adenoviruses, adeno-associated viruses, and herpes simplex viruses; bacteriophages; cosmids; plasmid vectors; fungal vectors; synthetic vectors; and other recombination vehicles typically used in the art. These vectors have been described for expression in a variety of eukaryotic and prokaryotic hosts and may be used for protein expression.

In a preferred embodiment, the vector comprises a nucleic acid sequence coding for a selective marker according to the invention, operatively linked to an expression control sequence. Selection of appropriate control sequences is dependent on the target cell used and the choice is within the skill of one in the art. Examples of expression control sequences, also referred to as regulatory sequences, include promoters, enhancers, polyadenylation signals, RNA polyrnerase binding sequences, sequences conferring inducibility of transcription and other expression control elements, such as scaffold attachment regions (SARs).

The promoter may be either a prokaryotic or eukaryotic promoter. Additionally the promoter may be a tissue specific promoter, inducible promoter, synthetic promoter, or hybrid promoter. More than one promoter may be placed in the construct. Examples of promoters include but are not limited to the phage lamda (PL) promoter; SV40 early promoter; adenovirus promoters, such as adenovirus major late promoter (Ad MLP); herpes simplex virus (HSV) promoter; a cytomegalovirus (CMV) promoter; such as the human CMV immediate early promoter; a long terminal repeat (LTR) promoter, such as a MoMLV LTR; the U3 region promoter of the Moloney murine sarcoma virus; Granzyme A promoter; regulatory sequences of the metallothioein gene; CD34 promoter; CD8 promoter; thymidine kinase (TK) promoters; B 19 parovirus promoters; and rous sarcoma virus (RSV) promoter. Additionally promoter elements from yeast and other fungi may be used, such as Gal 4 promoter and the alcohol dehydrogenase (ADH) promoter. These promoters are available commercially from various sources such as Stratagene (La Jolla, Calif.). It is to be understood that the scope of the present invention is not to be limited to a specific promoter.

The vector may further comprise a polyadenylation signal that is positioned 3' of the carboxy-terminal amino acid. Vectors containing both a promoter and a cloning site into which a polynucleotide can be operably linked are well known in the art. Such vectors are capable of transcribing RNA in vitro or in vivo, and are commercially available. Specific non-limiting examples include pSG, pSV2CAT, and pXt1 from Stratagene (La Jolla, Calif.) and pMSG, pSVL, pBPV and pSVK3 from Pharamacia. Other exemplary vectors include the pCMV mammalian expression vectors, such as pCMV6b and pCMV6c (Chiron Corporation, CA), pSFFV-Neo, and pBluescript-SK+. In order to optimize expression and/or in vitro transcription, it may be necessary to remove, add or alter 5' and/or 3' untranslated portions of polynucleotides to eliminate potentially extra inappropriate alternative translation initiation codons or other sequences that may interfere with or reduce expression, either at the level of transcription or translation. Alternatively consensus ribosome binding sites can be inserted immediately '5' of the start codon to enhance expression.

Particularly preferred vectors are retroviral vectors and reference is made to Coffin et al., "Retroviruses", (1997) Chapter 9 pp; 437–473 Cold Springs Harbor Laboratory Press. Retroviral vectors useful in the invention are produced recombinantly by procedures already taught in the art. WO94/29438, WO97/21824 and WO97/21825 describe the construction of retroviral packaging plasmids and packing cell lines. Common retroviral vectors are those derived from murine, avian or primate retroviruses. The most common retroviral vectors are those based on the Moloney murine leukemia virus (MoMLV) and mouse stem cell virus (MSCV). Vectors derived from MoMLV include, LMily, LINGFER, MINGFR, MND and MINT (Bender, et al., J. Virol. 61:1639–1649 (1987); Miller, et al., Biotechniques 7: 98–990 (1989); Robbins, et al., J. Virol. 71 :9466–9474 (1997) and U. S. Pat. No. 5,707,865). Vectors derived from MSCV include MSCV-MiLy (Agarwal, et al., J. of Virology 72:3720). Further non-limiting examples of vectors include those based on Gibbon ape leukemia virus (GALV), Moloney murine sacroma virus (MoMSV), myeloproliferative sarcoma virus (MPSV), murine embryonic stem cell virus (MESV), spleen focus forming virus (SFFV) and the lentiviruses, such as Human immunodeficiency virus (HIV-1 and HIV-2). New vector systems are continually being developed to take advantage of particular properties of parent retroviruses such as host range, usage of alternative cell surface receptors and the like (See C. Baum et al., Chapter 4 in Gene Therapy of Cancer Cells eds., Lattime and Gerson (1998)). The present invention is not limited to particular retroviral vectors, but may include any retroviral vector. Particularly preferred vectors include DNA from a murine virus corresponding to two long terminal repeats, and a packaging signal. In one embodiment the vector is a MoMLV or MSCV derived vector. In another preferred embodiment the vector is MND.

In producing retroviral vector constructs, the viral gag, pol and env sequence will generally be removed from the virus, creating room for insertion of foreign DNA sequences. Genes encoded by foreign DNA are usually expressed under the control a strong viral promoter in the long terminal repeat (LTR). While a LTR promoter is preferred, as mentioned above, numerous promoters are known.

Such a construct can be packaged into viral particles efficiently if the gag, pol and env functions are provided in trans by a packaging cell line. Therefore when the vector construct is introduced into the packaging cell, the gag-pol and env proteins produced by the cell, assemble with the vector RNA to produce infectious virions that are secreted into the culture medium. The virus thus produced can infect and integrate into the DNA of the target cell, but does not produce infectious viral particles since it is lacking essential packaging sequences. Most of the packaging cell lines currently in use have been transfected with separate plasmids, each containing one of the necessary coding sequences, so that multiple recombination events are necessary before a replication competent virus can be produced. Alternatively the packaging cell line harbors a provirus. (The DNA form of the reverse-transcribed RNA once its integrates into the genomie DNA of the infected cell). The provirus has been crippled so that although it may produce all the proteins required to assemble infectious viruses, its own RNA can not be packaged into virus. RNA produced from the recombinant virus is packaged instead. Therefore, the virus stock released from the packaging cells contains only recombinant virus. Non-limiting examples of retroviral packaging lines include PA12, PA317, PE501, PG13, ΨCRIP, RD114, GP7C-tTA-G10, ProPak-A (PPA-6), and PT67. Reference is made to Miller et al., Mol. Cell Biol. 6:2895 (1986); Miller, et al., Biotechniques 7:980 (1989); Danos, et al., Proc. Natl. Acad. Sci. USA 85:6460 (1988); Pear, et al., Proc. Natl. Acad. Sci. USA 90:8392 (1993); Rigg, et al., Virology 218: (1996); and Finer et al., Blood 83:43 (1994). Retroviral vector DNA can be introduced into packaging cells either by stable or transient transfection to produce vector particles.

Additionally preferred vectors include adenoviral vectors (See Frey et al., Blood 91:2781 (1998) and WO95/27071) and adeno-associated viral vectors (AAV) (See Chatterjee et al., Current Topics in Microbiol. and Immunol. 218:61 (1996). Reference is also made to Shenk, Chapter 6, 161–78, Breakefield et al., Chapter 8 201–235; Kroner-Lux et al., Chapter 9, 235–256 in Stem Cell Biology and Gene Therapy, eds. Quesenberry et al., John Wiley & Sons, 1998 and U.S. Pat. Nos. 5,693,531 and 5,691,176. The use of adenovirus derived vectors may be advantageous under certain situations because they are capable of infecting non-dividing cells, and unlike retroviral DNA, the adenoviral DNA is not integrated into the genome of the target cell. Further the capacity to carry foreign DNA is much larger in adenoviral vectors than retroviral vectors. The adeno-associated viral vectors are another useful delivery system. The DNA of these viruses may be integrated into non-dividing cells, and a number of polynucleotides have been successfully introduced into different cell types using adeno-associated viral vectors. The vectors are capable of transducing several cell types including hematopoietic cells and epithelial cells.

Vectors may also include hybrid vectors of AAV and adenoviruses as described in WO96/13598 and WO99147691 (The Trustees of the University of Pennsylvania), WO98/21345 (General Hospital), US5965441 (General Hospital), or WO99/58700 (Ariad Gne Therap.), the teaching of which being incorporated into the present invention in their entirety.

In one embodiment, the construct or vector will include not only a nucleic acid sequence encoding a mutated PTKR or a mutated EGFR as a selectable marker but also a second nucleic acid sequence encoding a heterologous gene to be transferred into a target cell. In a preferred embodiment the nucleic acid molecules are DNA. The term "heterologous" as it relates to nucleic acid sequences such as gene sequences denotes sequences that are not normally associated with a particular cell or vector and which are suitably inserted into a construct or vector under control of a promoter to permit expression in the target cell to be genetically modified. The heterologous gene may be located 5' or 3' to the selectable marker of the invention.

Non-limiting preferred vector constructs comprise the general structure as outlined below 5' to 3':

(a) LTR-X-I-M-LTR;
(b) LTR-M-LTR;
(c) LTR-M-(I)-X-LTR;
(d) LTR-X-pM-LTR; and
(e) LTR-X-I-M-SAR-LTR
  wherein LTR is a long terminal repeat, X is a heterologous gene for a desired protein, M is a selectable marker of the invention, I is an internal ribosomal entry site, SAR is a scaffold attachment region and p is a second promoter, preferably a CMV or PGK promoter.

A gene or coding sequence or a sequence that encodes a particular protein is a nucleic acid molecule that is transcribed and translated into a polypeptide in vitro or in vivo when placed under the control of appropriate regulatory sequences. The heterologous gene may be any gene for which expression is desired. Examples of heterologous genes include but are not limited to a therapeutic protein, a structural gene, a ribozyme, or an antisense sequence. The heterologous gene may be the entire protein or only the functionally active fragment thereof. The protein may include for example one that regulates cell differentiation or a therapeutic gene capable of compensating for a deficiency in a patient that arises from a defective endogenous gene. Additionally a therapeutic protein or gene may be one that antagonizes production or function of an infectious agent, antagonizes pathological processes, improves a host's genetic makeup, or facilitates engraftment.

Specific examples of a therapeutic gene or gene sequences are ones effective in the treatment of adenosine deaminase deficiency (ADA); sickle cell anemia; recombinase deficiency; recombinase regulatory gene deficiency; HIV, such as an antisense or trans-dominant REV gene; or a gene carrying a herpes simplex virus thymidine kinase (HSV-tk)). The heterologous gene may encode new antigens or drug resistant genes or may encode a toxin or an apoptosis inducer effective to specifically kill cancerous cells, or a specific suicide gene-to hematopoietic cells may be included. Additionally the heterologous gene may be a therapeutic gene that is non-human such as a yeast gene (Seo et al., Proc. Natl. Acad. Sci. 95:9167 (1998)).

The vector or construct may also comprise a second heterologous gene in addition to the first heterologous gene encoding a protein of interest. More than one gene may be necessary for the treatment of a particular disease. Alternatively more than one gene can be delivered using several compatible vectors. Depending on the genetic defect, the therapeutic gene can include regulatory and untranslated sequences. For human patients the therapeutic gene will generally be of human origin although genes of closely related species that exhibit high homology and biologically identical or equivalent function in humans may be used if the gene does not produce an adverse immune reaction in the recipient.

Nucleotide sequences of the heterologous gene encoding a protein of interest will generally be known in the art or can be obtained from various sequence databases such as GenBank. One skilled in the art will readily recognize that any structural gene can be excised as a compatible restriction fragment and placed in a vector in such a manner as to allow proper expression of the structural gene in target cells.

The target cells of the invention are mammalian cells and these include but are not limited to humans, mice, monkeys, chimpanzees, farm animals; such as cattle, sheep, pigs, goats, and horses, sport animals, pets; such as dogs and cats, and other laboratory rodents and animals; such as mice, rats, guinea pigs and the like. Preferably the target cells are human cells. Preferred human cells include liver, hematopoietic, smooth muscle, neural, endothelial vascular cells, tumor cells and epithelial cells. Hematopoietic cells are particularly preferred, and these cells encompass hematopoietic stem cells, erythrocytes, neutrophils, monocytes, platelets, mast cells, eosinophils and basophils, B and T lymphocytes, and NK cells as well as the respective lineage progenitor cells. Hematopoietic stem cells and T-cells are especially preferred. Hematopoietic stem cells (HSC) are defined as a population of hematopoietic cells containing long term multilineage repopulating potential. T-cells are defined as a type of lymphocyte and are thought to develop from hematopoietic stem cells. There are many types of T-cells including cytotoxic T-cells, helper T-cells, inducer T-cells and supressor T cells.

Methods of obtaining target cells, particularly hematopoietic cells are well known in the art and not repeated herein. Non-limiting sources of hematopoietic cells, including hematopoietic stem cells, are bone marrow, embryonic yolk sac, fetal liver tissue, adult spleen, and blood such as adult peripheral blood and umbilical cord blood. (To et al., Blood 89:2233 (1997)). Bone marrow cells may be obtained from ilium, sternum, tibiae, femora, spine and other bone cavities.

The manner in which target cells may be separated from other cells is not critical to this invention. Various procedures may be employed and include physical separation, magnetic separation using antibody-coated magnetic beads, affinity chromatography, and cytotoxic agents joined to a monoclonal antibody or used in conjunction with a monoclonal antibody. Also included is the use of fluorescence activated cell sorters (FACS) wherein the cells can be separated on the basis of the level of staining of the particular antigens. These techniques are well known to those skilled in the art and are described in various references including U.S. Pat. Nos. 5,061,620; 5,409,8213; 5,677,136; and 5,750,397; and Yau et al., Exp. Hematol. 18:219–222 (1990).

The order of cell separation is not critical to the invention, and specific cell types may be separated either prior to genetic modification with the mutated PTKR or after genetic modification. Preferably cells are initially separated by a coarse separation followed by using positive and/or negative selection. In humans the surface antigen expression profile of an enriched hematopoietic stem cell population may be identified by $CD34^+Thy-1^+Lin^-$. Other nonlimiting enriched phenotypes may include: $CD2^-$, $CD3^-$, $CD4^-$, $CD8^-$, $CD10^-$, $CD14^-$, $CD15^-$, $CD19^-$, $CD20^-$, $CD33^-$, $CD34^-$, $CD38^{lo/-}$, $CD45$, $CD59^{+/-}$, $CD71^-$, $CDW109^+$, glycophorin$^-$, $AC133^+$, $HLA-DR^{+/-}$, and $EM^+$. Lin$^-$ refers to a cell population selected on the basis of lack of expression of at least one lineage specific marker, such as, CD2, CD3, CD14, CD15 and CD56. The combination of expression markers used to isolate and define an enriched HSC population may vary depending on various factors and may vary as other express markers become available.

Murine HSCs with similar properties to the human $CD34^+Thy-1^+Lin^-$ may be identified by $kit^+Thy-1.1^{lo}Lin^{-/lo}Sca-1^+$ (KTLS). Other phenotypes are well known. When CD34 expression is combined with selection for Thy-1, a composition comprising approximately fewer than 5% lineage committed cells can be isolated (U.S. Pat. No. 5,061,620).

It has been shown that CD3 is expressed on most T cells, and that these cells can express the cell surface antigens CD2, CD4, and CD8 antigens. Also CD45 is a useful T cell marker. The most well known T cell marker is the T cell antigen receptor (TCR). There are presently two defined types of TCRs; α, β- TCR and γ, δ- TCR. B cells may be selected, for example, by expression of CD19 and CD20. Myeloid cells may be selected for example, by expression of CD14, CD15 and CD16. NK cells may be selected based on expression of CD56 and CD16. Erythrocytes may be identified by expression of glycophorin A. Neuronal cells may be identified by NCAM and LNGFR (Baldwin et al., J. Cell Biochein. 15:502 (1996)). Vascular endothelial cells may be identified by VEGFR2, CD34, P-Selectin, VCAM-1, ELAM-1, and ICAM-1.(Horvathova et al., Biol. Trace Elem. Res., 69: 15–26 (1999)). One skilled in the art is aware of other useful markers for the identification of other target cells.

Once a population containing the target cells are harvested and target cells, particularly hematopoietic cells, are separated, the cells are cultured in a suitable medium comprising a combination of growth factors that are sufficient to maintain growth. Methods for culturing target cells are well known to those skilled in the art, and these methods are only briefly mentioned herein. Any suitable culture container may be used, and these are readily available from commercial vendors. The seeding level is not critical and will depend on the type of cells used, but in general the seeding level for hematopoietic cells will be at least 10 cells per ml, more usually at least about 100 cells per ml and generally not more than $10^6$ cells per ml when the cells express CD34.

Various culture media, solid or liquid, can be used and non-limiting examples include DMEM, IMDM, X-vivo 15 and RPMI-1640. These are commercially available from various vendors. The formulations may be supplemented with a variety of different nutrients, growth factors, such as cytokines and the like. The medium can be serum free or supplemented with suitable amounts of serum such as fetal calf serum, autologous serum or plasma. If cells or cellular products are to be used in humans, the medium will preferably be serum free or supplemented with autologous serum or plasma. (Lansdorp et al., J. Exp. Med. 175:1501 (1992) and Petzer, et al. PNAS 93:1470 (1996). Also reference is made to Freshney, R. I., "Culture of Animal Cells, A Manual of Basic Techniques", Wiley-Liss, Inc. (1994)).

Non-limiting examples of compounds which may be used to supplement the culture medium are TPO, FL, KL, IL-1, IL-2, IL-3, IL-6, IL-12, IL-11, stem cell factor, G-CSF, GM-CSF, St1 factor, MCGF, LIF MIP-1α and EPO. These compounds may be used alone or in any combination, and preferred concentration ranges may be readily determined from the published art. When murine stem cells are cultured, a preferred non-limiting medium includes mIL3, mIL-6 and mSCF. Other molecules can be added to the culture media, for instance, adhesion molecules, such as fibronection or RetroNectin™ (commercially produced by Takara Shuzo Co., Otsu Shigi, Japan).

In vitro systems for measurement of mammalian stem cell activity include the long-term culture initiating cell assay (LTCIC) and the cobblestone-area-forming cell (CAFC) assay. (Pettengell, et al., Blood 84:3653 (1994); Breems et al., Leukemia 8:1095 (1994); Reading, et al., Exp. Hem. 22:786 (Abst # 406) (1994); and Ploemacher, et al., Blood 74:2755 (1989)). In the CAFC assay a sparsely plated cell population is simply tested for its ability to form distinct clonal outgrowths (or cobblestone areas) on a stromal cell monolayer over a period of time. This assay gives frequency readouts that correlate with LTCIC and are predictive of engraftment in in vivo assays and patients. A particularly preferred CAFC assay is described in Young, et al., Blood 88:1619 (1996). Flow cytometry can be used to subset hematopoietic cells from various tissue sources by the surface antigens they express. A combination of these assays may be used to test for hematopoietic cells or stem cells.

In one preferred embodiment the invention concerns a method of identifying genetically modified mammalian cells comprising introducing a nucleic acid sequence encoding a mutated protein-tyrosine kinase receptor (PTKR) as a selective marker and operatively linked to an expression control sequence into a target cell to form a genetically modified cell; allowing expression of the mutated PTKR in the genetically modified cell; and identifying said genetically modified cell expressing the mutated PTKR. In a preferred embodiment the selective marker is a mutated epidermal growth factor receptor (EGFR) family member, particularly preferred is a mutated EGFR1 and more specifically the sequences designated EGFR1-I and EGFR1-II. A polynucleotide or nucleic acid sequence is said to "encode" a polypeptide if, in its native state or when manipulated by methods well known to those of skill in the art it can be transcribed and/or translated to reproduce a polypeptide or fragment thereof. A construct or vector including a mutated PTKR of the invention may be introduced into the target population by any means of genetic transfer or modification known in the art.

The term "genetic modification" refers to any addition, deletion or disruption to a cells normal nucleotides and the methods of genetic modification are intended to encompass any genetic modification method of introducing nucleic acid sequences encoding the selective markers according to the invention and including but not limited to heterologous or foreign genes into mammalian target cells. These techniques are generally known. The term introducing is broadly used herein, and includes for example inserting. The term genetic modification includes but is not limited to transduction (viral mediated transfer of host DNA from a host or donor to a recipient, either in vivo or ex vivo), transfection (transformation of cells with isolated viral DNA genomes), liposome mediated transfer, electroporation, calcium phosphate transfection and others. Methods of transduction include direct co-culture of cells with producer cells (Bregni, et al., Blood 80:1418–1422 (1992)); culturing with viral supernatant alone, with or without appropriate growth factors and polycations (Xu, et al., Exp. Hemat. 22:223–230 (1994), and spinoculation.

In a preferred embodiment the mutated PTKRs of the invention and particularly the mutated EGFR markers are introduced into target cells by transduction with a retroviral vector as previously described. The host cell range that may be infected is determined by the viral envelope protein. The recombinant virus can be used to infect virtually any other cell type recognized by the env protein provided by the packaging cell, resulting in the integration of the viral genome in the transduced cell and the stable incorporation of the foreign gene product. In general, murine ecotropic env of MoMLV allows infection of rodents cells, whereas amphotropic env allows infection of rodent, avian and primate cells including human cells. Amphotropic packaging of cell lines for use with retroviral systems are known in the art and are commercially available. These include but are not limited to, PA12, PA317, ΨCRIP, and FLYA13. (See Miller, et al., Mol. Cell Biol. 5:431–437 (1985); Mill, et al., Mol. Cell Biol. 6:2895–2902 (1986); and Danos, et al. (1988) Proc. Natl. Acad. Sci. USA 85:6460–6464. Recently, the G-glycoprotein from vesicular stomatitis virus (VSV-G) has been substituted for the MoMLV env protein. (See Burns, et al., Proc. Natl. Acad. Sci. USA 90:8033–8037 (1993); and WO92/14829). Xenotropic vector systems also exist which allow infection of human cells.

Once the target cells are genetically transformed with a nucleotide sequence including the mutated PTKR as a marker, and optionally a heterologous gene, the modified cells expressing the mutated PTKR selectable marker may be identified by numerous techniques. The term "identify or "identification" used herein in reference to genetically modified cells, unless otherwise indicated means to mark, to purify, to enrich, to select, to isolate, or to separate. Identification can be by a single or multiple steps.

In a preferred embodiment, the genetically modified cells expressing the selective marker according to the invention are identified by an antibody that specifically recognizes and binds to the selectable marker, and particularly an antibody that recognizes a mutated EGFR. This kind of antibody has been described by O'Rourke, et al., Oncogene, 16:1197–1207 (1998). A secondary antibody may then be used to further identify or select the antibody coated cells, if the secondary antibody is coupled to either a fluorophore or immnuno-magnetic beads. The marker gene expressing cells may then be selected by flow cytometry or a by using a magnet to select bead-coated cells.

The techniques used for the identification of genetically modified cells expressing a selective marker of the invention include those described above and other well known techniques including but are not limited to inmunoselection; nucleotide detection by northern blots wherein RNA bound to a solid support is analyzed for binding to a liquid phase DNA; nucleotide detection by southern blots, wherein genomic DNA bound to a solid support is analyzed for binding to a liquid phase DNA; PCR amplification of genomic DNA; protein detection by western blots whereby protein bound to a solid support is analyzed for binding to a liquid phase antibody; reverse transcription of MRNA and amplification with PCR; and FISH wherein chromosomes are analyzed by Fluorescence in situ hybridization with a liquid phase DNA (Lawrence, et al., Science, 249(4971):928–932 (1990)).

The above listed methods are not described in detail herein; they are well known by those of ordinary skill in the art. In brief, antibodies may be obtained by methods well known and reference is made to Harlow, et al., "Antibodies: A Laboratory Manual: (1988), Biosupplynet Source Book, (1999) Cold Springs Harbor Laboratory. Either polyclonal antibodies that are reactive to the antigen of interest may be used or monoclonal antibody producing cell clones may be generated. According to the invention the antibody must recognize the extracellular domain of the mutated PTKR selective marker. More particularly if parts of the extracellular domain are modified, by for example deletion, the antibody should recognized an epitope of the remaining amino acid sequence of the mutated PTKR.

Monoclonal antibodies to EGFR are available commercially. Some sources include Calbiochem (CA), Pharmingen (CA), Becton Dickinson (CA), and the American Type Culture Collection (ATCC) (Virginia). The antibody may be identified and assayed in vitro by a range of methods including gel diffusion, immunoassay, immunoelectrophoresis and immunofluorescence. Once genetically modified cells are labeled they can be incubated with an antibody against the mutated receptor.

The genetically modified cells may be physically separated by the use of antibodies, flow cytometry including fluorescence activated cell sorting (FACS), and bead selection. (U.S. Pat. No. 5,011,912).

In FACS an antibody that recognizes the mutated PTYR may be used to identify the cells that express the PTKR. This primary antibody can be conjugated to a fluorophore, such as fluorescein isothiocyanate (FITC), phycoerythrin (PE), cy-chrome (CyC), allophycocyanine (APC), tricolor (TC) or Texas Red (TX). If the primary antibody is not conjugated to a fluorophore a secondary antibody that is conjugated to a fluorophore may be introduced into the cell sample containing cells which have expressed the mutated PTKR and which are recognized by the primary antibody. The primary antibody is attached to the mutant PTKR. The secondary antibody binds to the primary antibody and cells having the secondary antibody can be induced to fluoresce. Separation may be achieved by the fluorescence activated cell sorter.

The genetically modified target cells expressing a mutated PTKR, and optionally a second nucleic acid sequence encoding a protein of interest may be expanded, either prior to or after identification and selection, by culturing the cells for days or weeks in appropriate culture media, with or without supplements by means well known in the art. (Freshney supra, Celis supra, and Coligan et al., supra).

The genetically modified marked cells obtained according to the methods of the invention may further be used in an autologous or allogeneic setting wherein the genetically modified target cells, preferably hematopoietic cells are expanded and then used in gene therapy for example in bone marrow transplantation, graft facilitation, or immune reconstitution. The expanded cells expressing the mutated cell surface marker may be infused into a subject. Samples may be taken and then tested for the selectable marker by FACS analysis, PCR, or FISH, as referenced above, to determine the persistence of the marked cells and further to assess efficiency of transduction.

The invention generally described above will be more readily understood by reference to the following examples, which are hereby included merely for the purpose of illustration of certain embodiments of the present invention and are not intended to limit the invention in any way.

EXAMPLE 1

A. Isolation of Human EGFR cDNAs

EGFR cDNA is isolated by PCR from cDNA that has been generated from colorectal adenocarcinoma: SW480 cell line (Marathon cDNA, Clontech (CA); Leibowitz, et al., Cancer Research 36:4562–4569 (1976). The following primers are used in the described methods and were obtained from Life Technologies (Md.):

5' Primers:

| | |
|---|---|
| EGFR1 | CTA GGC TAG CAT GCG ACC CTC CGG GAC GGC C SEQ ID NO. 3 |
| EGFR2 | CTC TGC CCG GCG AGT CGG GCT GAC AGC TAT GAG ATG GAG GAA SEQ ID NO. 4 |
| 3' Primers: | |
| EGFR3 | TTC CTC CAT CTC ATA GCT GTC AGC CCG ACT CGC CGG GCA GAG SEQ ID NO. 5 |
| EGFR220R | GGA TAT CCT ACG TGC GCT TCC GAA CGA TGT G SEQ ID NO. 6 |

B. Generation of EGFR1-I

The primers EGFR1 and EGFR2220R are used to generate an intracellular deletion mutant of EGFR (FIGS. 2 and 3) from the SW480 adenocarcinoma cell line cDNA. Amino acid residues 679–1210 of the sequence in FIG. 2 (SEQ ID NO. 2) are deleted, and this mutant EGFR is designated EGFR1-I.

The 5' primer EGFR1 covers the start codon of the EGFR. The 3'-primer EGFR2220R contains a stop codon in place of amino acid 679 of the SEQ ID NO. 2 (FIG. 2). Using primers EGFR1 and EGFR2220R results in the amplification of the EGFR sequence that has a deletion of amino acids 679 to 1210.

The following PCR reaction is performed: Marathon cDNA (~0.5 ng) is mixed with Advantage cDNA buffer (10 mM Tris-HCl (pH=7.5 at 42° C.), 50 mM KCl, 2.5 mM MgCl2, 0.001% Gelatin, 2.5 $\mu$mol dATP, 2.5 $\mu$mol dCTP, 2.5 $\mu$mol dGTP, 2.5 $\mu$mol dTTP), 0.01 $OD_{260}$ primer EGFR1, 0.01 $OD_{260}$ primer EGFR2220R, 1 $\mu$l Advantage cDNA polymerase (Life Technologies; MD), 5U Pfu Turbo polymerase (from Pyrococcus furiosus) (Promega; WI) and water in a final volume of 50 $\mu$l. PCR is performed as follows: Cycle 1: 95° C. for 5 min, Cycle 2–15: 95° C. for 1 min, 60° C. for 1 min, 68° C. for 4 min, and Cycle 16: 68° C. for 10 min.

The reaction is then cooled to 4° C. in the PCR machine and subsequently the amplified cDNA is ethanol precipitated with 0.3 M sodium acetate. The pellet is washed once with 70% ethanol, dried and resuspended in 50 $\mu$l $H_2O$.

1 µl of the above PCR reaction is then reamplified, and the reaction mix contains for the second round of amplification in addition to 1 µl of the above PCR reaction: Pfu buffer (20 mM Tris-HCl (pH8.8), 2 mM $MgSO_4$, 10 mM KCl, 10 mM $(NH_4)_2SO_4$, 0.1% Triton X-100, 0.1 mg/ml BSA), 2.5 µmol of each dNTP (dATP, dTTP, dCTP, dGTP), 0.01 $OD_{260}$ primer EGFR1, 0.01 $OD_{260}$ primer EGFR2220R, 5 U Pfu Turbo Polyrnerase and water in a final volume of 50 µl. PCR is performed as follows: Cycle 17: 95° C. for 5 min, Cycle 1848: 95° C. for 1 min, 60° C. for 1 min, 72° C. for 4 min, and Cycle 49: 72° C. for 10 min.

The reaction is cooled to 4° C. in the PCR machine and the amplified cDNA is ethanol precipitated with 0.3 M sodium acetate. The pellet is washed once with 70% ethanol, dried and resuspended in 20 µl $H_2O$. The PCR reaction is loaded on a 1×TAE gel. A band with the size of approximately 2200 bp is isolated from the gel and cloned into the SrfI restriction site of pPCR-Script Amp vector (Stratagene; CA) according to the manufacturer's protocol. The resulting vector is called pPCR-Script EGFR1-I. The correctness of the subeloned PCR product is confirmed by restriction analysis and sequencing according to well known methods.

C. Generation of EGFR1-II

EGFR1-II contains the same deletion in the intracellular domain as EGFR1-I (a stop codon in position 679). In addition, amino acids 25 to 312 are deleted in the extracellular domain of EGFR depicted in FIG. 2 (SEQ ID NO. 2). The sequence of the signal peptide, amino acid 1 to 24, is fused to amino acid 313 of the EGFR extracellular domain. In order to delete the EGFR extracellular domain, a protocol is used that is described in further detail below. (Also see White, ed. Methods in Molecular Biology, Vol 15. PCR Protocols, Chapter 25 (1993)). This method is known in the art as "gene splicing by overlap extension (gene SOEing)". (FIG. 4)

Primer pairs EGFR1I/GFR3 and EGFR2/EGFR2220R are used to amplify 2 PCR products (a) and (b). Primer EGFR1 encodes amino acid 1 to 7, and Primer EGFR3 encodes amino acid 18 to 24 fused to the nucleotide sequence of amino acid 313 to 319. Using the EGFR1 and EGFR3 primers a PCR product is generated that encodes amino acid 1 to 24 which is fused to amino acid 313 to 319.

Primer EGFR2 encodes the same amino acid acids as Primer EGFR3 only in the reverse orientation. Primer EGFR2220R encodes a stop codon in place of amino acid 679. As described in section B above, this results in the deletion of the intracellular domain after amino acid 678.

Using these two primer pairs, two PCR products (a) and (b), are obtained each having a 42 nucleotide of overlapping sequence encoding amino acid 18 to 24 and amino acids 313 to 319 (FIG. 4—PCR reaction 1).

In the second PCR reaction, primers EGFR1 and EGFR2220R are used with the intermediate PCR products (a) and (b). When these intermediate PCR products are mixed, denatured and reannealed, one of the strands of the two PCR products can overlap at their 3' ends, and act as primers on one another to make the mutant product. Subsequently, the mutant PCR product (c) is amplified with the primers EGFR1 and EGFR2220R. The resulting PCR product encodes EGFR1-II amino acid 1 to 24 of the wt EGFR fused to amino acids 313 to 678 of the wt EGFR with a stop codon in position 679 (FIG. 4).

The PCR reactions are as follows: The first PCR reaction in: a.) 0.01 $OD_{260}$ of EGFR1 and 0.01 $OD_{260}$ of EGFR3 and in b.) 0.01 $OD_{260}$ EGFR2 and 0.01 $OD_{260}$ EGFR2220R are mixed with ~0.4 ng Marathon cDNA, 1×Advantage cDNA Polymerase buffer (as described in B), 1 µl Advantage cDNA polymerasc, 2.5 µmol of each dNTP, 5U Pfu Polymerase (Promega) and $H_2O$ in a final volume of 50 µl. The PCR is performed as follows: Cycle 1: 94° C. for 5 min, Cycle 2–16: 94° C. for 0.5 min, 60° C. for 1 min, 68° C. for 7 min, and Cycle 17: 68° C. for 10 min.

The reactions are cooled to 4° C. in the PCR machine and the amplified PCR products are ethanol precipitated with 0.3 M sodium acetate. The pellets are washed once with 70% ethanol, dried and resuspended in 50 µl $H_2O$.

5 µl of each PCR reaction (a) and (b) are then further amplified. The reaction mix contains for the second round of amplification, in addition to each PCR reaction (a) 0.01 $OD_{260}$ of primers EGFR1 and EGFR3 or (b) 0.01 $OD_{260}$ of primers EGFR2 and EGFR2220R: 1×Pfu buffer, 2.5 µmol of each dNTP, and 5 U Pfu Polymerase (Promega; WI) and $H_2O$ in a final volume of 50 µl. The PCR is performed as follows: Cycle 18: 94° C. for 5 min, Cycle 19–49: 94° C. for 0.5 min, 60° C. for 1 min, 72° C. for 6 min and Cycle 50: 72° C. for 10 min.

The reactions are then cooled to 40C in the PCR machine and the amplified PCR products are phenol/chloroform extracted and ethanol precipitated with 0.3 M sodium acetate. The pellet is washed once with 70% ethanol, dried and resuspended in 20 µl $H_2O$.

In a second PCR reaction, PCR product (a) and (b) are mixed in equimolar amounts and reamplified with Pfu Turbo Polymerase (Stratagene) using the primer pair EGFR1 and EGFR2220R. The PCR mix is the same as described for cycles 18–50. The PCR is performed as follows: Cycle 1: 95° C. for 5 min, Cycle 2–32: 95° C. for 1 min, 60° C. for 1 min, 72° C. for 4 min, and Cycle 33: 72° C. for 10 min. The PCR is then loaded on a gel (as described above) and a band of ~1200 bp is isolated. This PCR product is cloned into the SrfI site pPCR-Script (Stratagene; CA) according to the manufacturer's protocol. The resulting vector is called pPCR-Script EGFR1-II. The correctness of the subcloned PCR product (c) is confirmed by restriction analysis and sequencing according to well known methods.

D. Generation of Retroviral Vectors Containing Mutated EGFRs and Viral Spernatants EGFR1-I and EGFR1-II sequences are excised from pPCR-Script EGFR-I and pPCR-Script EGFR-II using the restriction sites NotI and XhoI and are cloned into the multiple cloning site of the Murine Leukemia Virus (MoMLV) based retroviral vector pG1a (GTI, Maryland)—(pG1a-mutated sequence—IRES—nerve growth factor receptor (NGFR)), which has been cut with NotI and XhoI. The retroviral vectors are designated pG1a EGFR1-I and pG1aEGFR1-II.

The constructs are cotransfected into human embryonic kidney cells 293T (293T cells) (Gary Nolan, Stanford) with an envelope construct pCiGL that permits expression of the Vesicular Stomatitis Virus G-Protein (VSV-G envelope) under the control of the cytomegalovirus (CMV). Also cotransfected into 293T cells is the packaging construct pCiGP (encoding MoMLV gag-pol under the control of the CMV promoter) using the $CaCl_2$ technique (Clontech; CA). (WO 97/21825 and Rigg, et al., Virology 218:290–295 (1996)).

Viral supernatants are collected 24, 48, and 72 hours after transfection, centrifuged at 1200 rpm in a Beckmnan GS-6KR centriftige to remove particulate material, and either used immediately to transduce cells or frozen in a dry ice/methanol bath. The viral supernatants are used to transduce the packaging cell line ProPak-A-6 (PPA-6) (Systemix, Inc.). The PPA-6 cell line is a derivative of 293T cells expressing the MLV amphotropic envelope and MLV gag/pol under the control of the CMV promoter (Rigg et al. supra). The PPA-6 cells are sorted by immuno-magnetic bead selection. Alternatively, if the cells only expressed low amounts of mutated EGFR, the cells are sorted by FACSorting as described in detail below. Supernatants from PPA-6 cells are collected on day 2, 3 and 4 after transduction and treated as described for 293T cells. The generated supernatants of PPA6 cells contain recombinant viral particles that have the amphotropic envelope and are used to transduce human primary cells and cell lines.

E. Tissue Culture and Cell Lines

The following cell lines and primary cells are used: (a) human T cell line, CEMSS (Frederico, et al., J. Biol. Regul. Homeost Agents, 7: 41–49 (1993)), (b) human embryonic kidney cells 293T (293T) (Pear, et al., Proc. Natl. Acad. Sci. USA 90:8392–8396 (1993)), and (c) PPA-6 (Rigg, et al., supra). Human primary T cells are obtained by isolating the mononuclear cell fraction from human blood using Ficoll-gradient centrifugation (Noble and Cutts, Can. Vet. J. 8: 110–111 (1967) and Boyle and Chow, Transfusion 9:151–155 (1969). Human blood (buffycoats; Pietersz, et al., Vox Sang 49: 81–85 (1985) and Pietersz, et al., Blut. 54:201–206 (1987) obtained from the Stanford Bloodbank are diluted 1:1 with phosphate buffered saline (PBS). In 50 ml tubes, 15 ml blood are overlaid onto 21 ml of Ficoll (Isoprep; Robbins Scientific, California). The gradient is spun for 30 minutes at 1700 rpm in a Beckman GS-6KR at room temperature and stopped without using the break. Peripheral blood mononuclear cells (PBMCs) are collected from the interface of the Lymphoprep gradient. The resulting PBMCs are further purified on a second Ficoll gradient to remove remaining blood cells. The PBMCs are incubated for 1 hour in a tissue culture flask in tissue culture media for PBMCs (see below) at 37° C. in 5% $CO_2$ allowing adherent cells such as macrophages to attach to the tissue culture flask. Non-adherent cells (T/B/NK cells) are used to purify $CD4^+$ T cells. Cells ($2 \times 10^8$) are incubated with 300 µl anti-CD4 antibody for 1 hour at 4° C. The cells are washed 3 times with PBS and incubated with $1 \times 10^8$ anti-mouse IgG coupled immuno-magnetic beads (Dynal, Oslo) for 1 hour at 4° C. The $CD4^+$ cells that bound the CD4-antibodies and the secondary antibody coupled magnetic beads are positively selected by incubating the cells for 10 minutes on a Dynal magnet. After removing the unbound cells, the remaining cells are taken off the magnet and put into culture (see below). Usually the beads remain for up to 10 days on the cells.

$CD34^+$ cells are isolated from G-CSF mobilized peripheral blood (MPB) using Isolex 300SA or 300I (Baxter, IL) (Systemix, CA). The cells are approximately 80–90% pure.

Cells are cultured in a Steri-Cult 200 incubator (Forma-Scientific) at 5% $CO_2$. Media (DMEM, Iscove's medium RPMI), PBS, and sodium pyruvate are obtained from JRH Biosciences (CA), FBS from Hyclone (Utah), L-glutamine, Trypsin and MEM vitamins from Life Technologies (Maryland), ITS (insulin/transferrin/sodium selenite), PHA (phythemaglutinin), Interleukin-2 (I1-2) from Sigma (Missouri).

The cells are cultured in DMEM, 10% FBS, 1% sodium pynivate, 1% L-glutamine (293 T, PPA-6); RPMI, 10% FBS, 1% sodium pyruvate, 1% L-glutamine (CEMSS), Iscove's medium 10% FBS, 1% L-glutamine, 1% ITS (insulin/transferrin/sodium selenite, 0.5 mg/ml stock), 1% MEM vitamins (human PBMCs). $CD4^+$ T cells are stimulated every 10–12 days with 1–2 µg/ml PHA, irradiated feeder cells and 40 U/ml Il-2.

Irradiated feeder cells are generated as follows: PBMCs are isolated as described above and irradiated with 3500 rads. The cells are mixed at a 10:1 ratio with the B cell lymphoma JY (Barbosa, et al., Proc. Natl. Acad. Sci. 81:7549–7553 (1984)) that had been irradiated with 6000 rads.

To obtain T-cells in a resting state, 4–5 days after stimulation T cells are transferred into fresh medium that contained 20 U/ml Il-2. $CD34^+$ cells are grown in X vivo 15, 50 ng/ml thrombopoietin) (TPO; R & D Systems, MN), 100 ng/ml flt-3 ligand (FL), 100 ng/ml steel factor (SF). (SyStemix, Inc.)

In order to passage adherent cells, the cells are washed once with PBS, then trypsinized for 5 min and subsequently split into new tissue culture flasks (VYWR, New Jersey).

F. Transduction of PPA-6, Human T Cell Lines, Primary T Cells and $CD34^+$ Cells $10^6$ cells/ml from step (E) are transduced with 1–3 ml of viral supernatant, that has been either generated from 293 T cells or PPA-6 cells, by spinoculation with 8 µg/ml protamine sulfate (Sigma, Missouri). Spinoculation is done at 37° C. for 3 hrs at 3000 rpm ($CD34^+$ cells, PPA-6) or at 2750 rpm (human T cells, CEMSS). PPA-6 cells are transduced in 6 well plates, non adherent cells in 6 ml tubes (VWR). Human T cells and $CD34^+$ cells are activated for 2 days prior to the transduction procedure with PHA/IL-2 or TPO/FL/SF, respectively.

G. FACS Analysis, FACSsorting and Immuno-magletic Bead Selection of Cells expressing EGFR1-I and EGFR1-II The following antibodies and reagents are used for staining. CD4-FITC (Caltag; CA), anti-CD34-APC (Becton Dickinson; NJ), Thy-1-PE (Becton Dickinson), propidium iodide (PI) (Sigma), unconjugated anti-EGFR antibody (GR01) (Calbiochem; CA), goat anti-mouse IgG-PE/FITC (Caltag), goat anti-mouse $IgG_2a$-PE/FITC (Caltag), and anti-mouse IgG coupled magnetic beads (Dynal; Oslo). The anti-bodies and immuno-magnetic beads were used according to manufacturer's protocol. $1 \times 10^6$ cells are stained in 50 µl of PBS/2% FBS for 20 to 60 minutes at 4° C. When a secondary antibody is used the cells are washed once with 2 ml of PBS/2% FBS, then incubated again in 50 µl PBS/2% FBS and the secondary antibody is added. Before FACS analysis, the cells are again washed once with PBS/2% FBS, centrifuged and then resuspended in 500 µl PBS/2% FCS containing 1 µg/ml PI. FACS analysis is performed on a FACSscan (Becton-Dickinson Immunocytometry Group; CA) according to manufacturer's instructions.

Cells that express the marker genes, EGFR1-I and EGFR1-II are sorted as follows: $2 \times 10^7$/ml PBS/2% FBS cells are stained with an anti-EGFR antibody (at least with 1 µl antibody/$10^6$ cells; GR01). The cells are washed twice with PBS/2% FBS and subsequently incubated with a fluorophore (FITC, PE) conjugated rat anti-mouse IgG antibody (5 µl/$10^6$ cells) that recognizes the anti-EGFR antibody. The cells are also stained with PI to distinguish between dead and live cells. $1 \times 10^6$ cells/ml are sorted for EGFR-positive and PI-negative cells. This is done on a FACSstar Plus (Becton-Dickinson Immunocytometry Group) according to manufacturer's protocol.

To isolate cells by bead selection, the cells are stained with an anti-EGFR antibody. The $10^7$ cells/ml are incubated with 10 μl/ml anti-EGFR antibody (GR01) in PBS/2% FBS for 1 hr on ice with occasional shaking. The cells are washed 3 times with PBS/2% FCS and then anti-IgG antibody coupled magnetic beads (Dynal; Oslo) that can recognize the anti-EGFR antibody are added (~5 beads per positive cell). Again the cells are incubated for 1 hr on ice. The cells that express EGFR are selected by positive selection with a Dynal magnet (Dynal; Oslo) for 10 min. The unbound cells are removed and the EGFR expressing cells are put into culture (see section E.).

Figure 5:
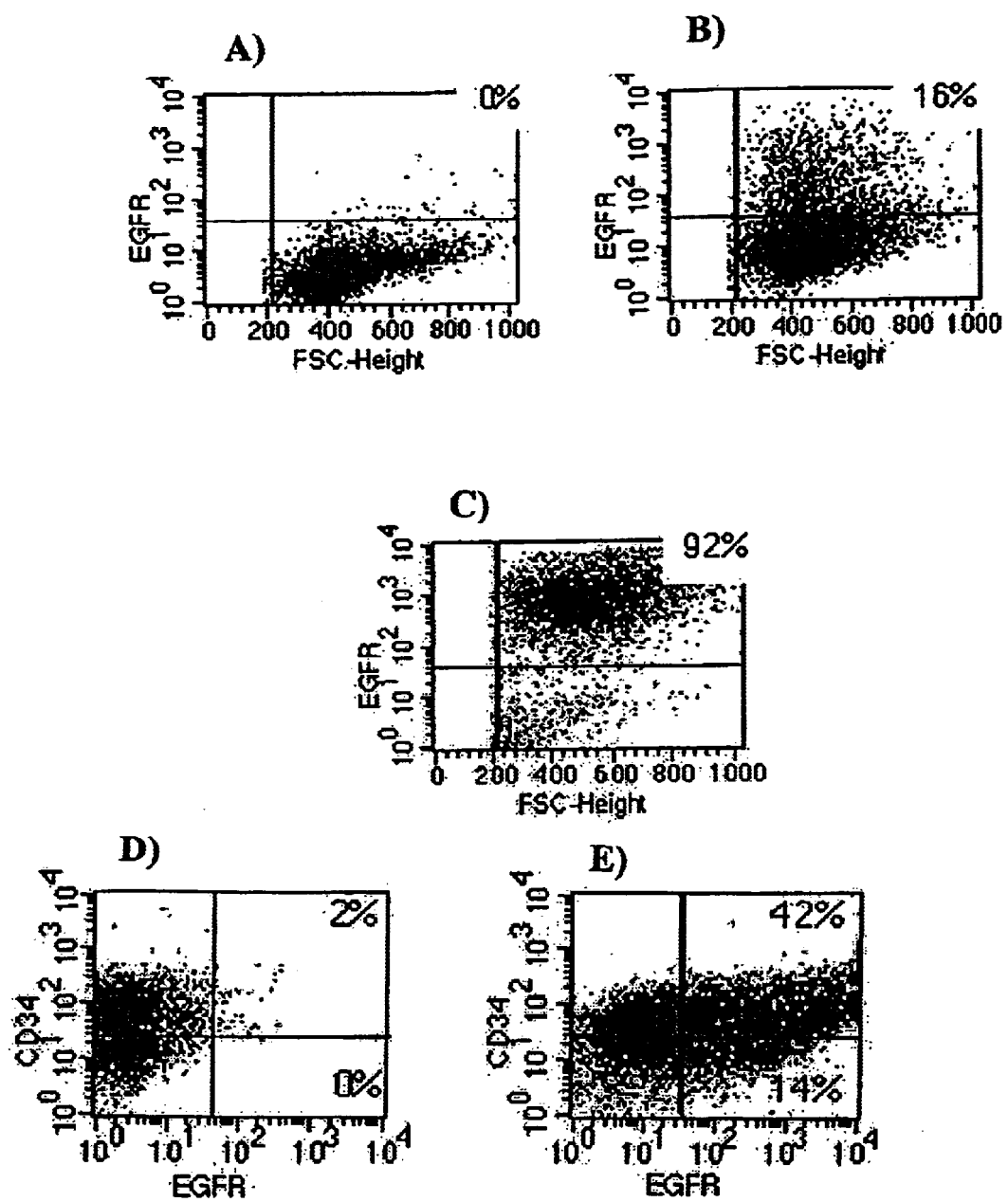
FIG. 5 illustrates expression of EGFR1-II on primary T cells and CD34$^+$ cells after transduction with supernatants that were generated from PPA-6 cells. Panel A corresponds to untransduced cells, panel B illustrates expression after transduction and panel C illustrates expression after immuno-magnetic beadselection for mutated EGFR expression on T-cells. Panel D corresponds to untransduced cells and panel E illustrates expression of CD34$^+$ cells.

FIG. 5 illustrates the expression of EGFR1-II CD34+ cells after transduction of these cells with supernatants that are generated from PPA-6 cells. Primary human T cells are transduced with PPA-6 supernatants and are selected by immuno-magnetic beadselection then sorted using a FACStar Plus (data not shown). The cells are enriched from 16% to 92%.

EXAMPLE 2

A. Isolation of Human MuSK-R cDNAs

MuSK-R is isolated by PCR from fetal skeletal muscle cDNA (Marathon cDNA, Invitrogen) using primers flanking the 5' and 3' of the MuSK-R cDNA.

The following primers obtained from Operon Technologies, Inc. are used to amplify MuSK-R cDNA:

| MuSK21FN: | CGT CCT GCG TGA GCC TGG ATT AAT C | SEQ ID NO: 9 |
|---|---|---|
| MuSK34FN: | GCC TGG AFF AAT CAT GAG AGA GCT C | SEQ ID NO: 10 |
| MuSK2666RN: | CGA GGC CTG TCT TCA ACC TTA GAC ACT CAC AGT TCC CTC TGC | SEQ ID NO: 11 |

The 5' primer MuSK21FN covers 25 nucleotide (nt) before the start codon, the second 5' primer MuSK34FN covers the start codon (aa 1) of MuSK-R and surrounding sequence. The 3'-primer MuSK2666RN covers the stop codon of MUSK-R and surrounding sequence. Using primers MuSK21FN, MuSK34FN and MuSK2666RN results in the amplification of a DNA fragment of ~2600 bp that encodes a MuSK-R wt protein.

The following PCR reaction is performed: Marathon cDNA (~2 ng) is mixed with Advantage cDNA buffer (10 mM Tris-HCl (pH=7.5 at 42° C.), 50 mM KCl, 2.5 mM $MgCl_2$, 0.001% Gelatin), 2.5 μmol dATP, 2.5 μmol dCTP, 2.5 μmol dGTP, 2.5 μmol TTP), 1 μg primer MuSK21FN, 1 μg primer MuSK2666RN, 1 μl Advantage cDNA polymerase, and water in a final volume of 50 μl. The PCR is performed as follows: Cycle 1: 94° C. for 5 min, Cycle 2–11: 94° C. for 0.5 min, 63° C. for 1 min, 68° C. for 6 min, and Cycle 12: 68° C. for 10 min.

The reaction is cooled to 4° C. in the PCR machine, and the amplified cDNA is ethanol precipitated with 0.3 M sodium acetate. The pellet is washed once with 70%/o ethanol, dried and resuspended in 100 μl $H_2O$.

10 μl of the above PCR reaction is then reamplified. The reaction mix contains for the second round of amplification step in addition to 10 μl of the above PCR reaction: Pfu buffer (20 mM Tris-HCl (pH8.8), 2 mM $MgSO_4$, 10 mM KCl, 10 mM $(NH_4)_2SO_4$, 0.1% Triton X-100, 0.1 mg/ml BSA), 2.5 μmol of each dNTP (dATP, dCTP, dGTP, dTTP), 1 μg primer MuSK34FN, 1 μg primer MuSK2666RN, 5 U Pfu Turbo Polymerase (from Pyrococcus furiosus) and water in a final volume of 50 μl. The PCR is performed as follows: Cycle 13: 94° C. for 5 min, Cycle 14–43: 94° C. for 0.5 min, 62° C. for 1 min, 72° C. 6 min, and Cycle 44: 72° C. for 10 min.

The reaction is cooled to 4° C. in the PCR machine and the amplified cDNA is ethanol precipitated with 0.3 M sodium acetate. The pellet is washed once with 70% ethanol, dried and resuspended in 20 μl $H_2O$. The PCR reaction is loaded on a 1×TAE gel. A band with the size of ~2600 bp is isolated from the gel and cloned into the SrfI restriction site of pPCR-Script Amp vector (Stratagene, CA) according to the manufacturer's protocol. The resulting vector is called pPCR-Script MuSK-R-wt. The correctness or the subcloned PCR product is confirmed by restriction analysis and sequencing by methods well known in the art. (The nucleotide sequence is illustrated in SEQ ID NO.7).

B. Generation of Mutations in the Intracellular Domain of MuSK-R by PCR

The primers MuSK1380F, MuSK1657R, and 1747R are used to generate intracellular deletion mutants of MuSK-R from the plasmid pPCRScriptMuSK-R. The primer sequences are as follows wherein p means phosphorylated:

| Primer 1380F: | 5' pCG GCC TGT GCC AGA CTG CCA CAT CTA G | (SEQ ID NO: 12); |
|---|---|---|
| Primer 1657R: | 5' pCG TCT AGG TGA GGG TTA CTG CTG CTG ATT CTC | (SEQ ID NO:13) |
| Primer 1747R: | 5' pGG TTA ACC CTA TTC AAT GTT ATT CCT TGA ATA CTC CAG | (SEQ ID NO: 14). |

Using primer pair MuSK1380F and 1657R results in the deletion of amino acid residues 538–879 of MuSK-R, using primer pair MuSK1380F and 1747R results in the deletion of amino acid residues 577–879. The two mutant forms of MuSK-R are designated MuSK-RΔ538–879 (MuSK-RI) and MuSK-RΔ577–879 (MuSK-RII). In both MUSK-RI and MuSK-RII most of the intracellular domain of MuSK-R as shown in FIG. 6 is deleted. While not meant to limit the invention in any manner, it is believed that both truncations result in a deletion of the kinase domain and most of the substrate binding motifs of the wt MUSK-R illustrated in FIG. 6.

The 5' primer MuSK1380F covers the nucleotide sequence 1333–1410 of the MuSK-R. The 3'-primers MuSK1657R and 1747R contain stop codons in place of amino acid 538 and 577 of MuSK-R. Using primer MuSK1380F with MuSK1657R or MuSK1747R results in the amplification of MuSK-R nucleotide sequence 1333 to 1614 that has a stop codon in the position of amino acid 538 or nucleotide sequence 1333–1728 that has a stop codon in the position of amino acid 577, respectively. The PCR reaction includes ~10 ng hMuSK-R wt DNA, 1×Pfu buffer, 1 μg of primer MuSK138OF and either 1 μg primer MuSK1657R or MuSK1747R, 2.5 μmol of each dNTP, 5 U Pfu polymnerase and $H_2O$ in a final volume of 50 μl. The PCR reaction is performed as follows: Cycle 1: 95° C. for 5 min, Cycle 2–31: 95° C. 0.5 min, 60° C. for 1 min, 72° C. for 4 min, Cycle 32: 72° C. for 10 min. The PCR reaction is cooled to 4° C. in the PCR machine and then loaded on a 1×TAE gel.

The two PCR products MuSK-RI (nt 1380–1614) and MuSK-RII (nt 1380–1728) are cloned into the SrfI site of pPCR-ScriptAmp (Stratagene) according to the manufacturer's protocol. As the 5' coding sequence from MuSK (nt 1–1379) is missing in these constructs, this sequence is excised from the plasmid pPCR-Script MuSK-wt using restriction sites NaeI and AatII. The two pPCR-Script vectors containing the modified MuSK sequence nt 1–1614 and 1–1726 are called pPCR-Script-MuSK-RI and pPCR-Script MuSK-RII, respectively. The correctness of the vectors are confirmed by restriction analysis and sequencing by methods well known in the art.

C. Generation of Retroviral Vectors Containing Mutated MuSK-Rs and Viral Supernatants Wild-type and mutant MuSK-R are excised from pPCRScriptMuSK-Rwt, pPCRScriptMuSK-RI and pPCRScriptMuSK-RII using the NotI and XhoI site and are cloned into the multiple cloning site of the Moloney Murine Leukemia Virus (MoMLV) based retroviral vector pG1a (GTI, Maryland) which is cut with NotI and XhoI. The retroviral vectors are designated pG1aMuSK-R, pG1aMuSK-RI and pG1aMuSK-RII. The constructs pG1aMuSK-R, pG1aMuSK-RI and pG1aMuSK-RII were used to generate viral supernatants as described in Example 1.

D. Tissue Culture and Cell Lines

Experiments were carried out the same way as described in Example 1.

E. Transduction of PPA-6 and Human T Cell Line

Experiments were carried out the same way as described in Example 1.

F. FACS Analysis and Immuno-magnetic Bead Selection of Cells that Tress MUSK-RI and MUSK-RII In addition to the antibodies that are listed in Example 1, anti-MuSK-R polyclonal serum, and anti-MuSK-R hybridoma supernatant (see section G) were used for flow cytometry and immuno-magnetic bead selection.

In order to isolate cells by immuno-magnetic bead selection, the cells are stained with an anti-MUSK-R antibody. For this purpose the $10^7$ cells/ml are incubated with 1–3 ml anti-MuSK-R hybridoma supernatant in PBS/2% FBS for 1 hr on ice with occasional shaking. The cells are washed 3 times with PBS/2% FCS and then anti-IgG antibody coupled magnetic beads, that can recognize anti-MuSK-R antibodies, are added (~5 beads per positive cell). The cells are incubated for 1 hr on ice. Cells that express MuSK-R are selected by positive selection with a Dynal magnet (Dynal, Oslo) for 10 min. The unbound cells are removed and the MuSK-R expressing cells are put into culture as described in section D.

G. Generation of a Monoclonal Antibody against the Extracellular Domain of MuSK-R To generate monoclonal antibodies against the extracellular domain (XC) of MuSK-R, MuSK-R XC is amplified by PCR and cloned into the expression construct pSecTag2b (Invitrogen). Cloning the XC domain of MuSK-R into the multiple cloning site (MCS) of the plasmid pSecTag2b allows for the expression of the XC under the control of the CMV promoter. In addition, the plasmid contains the sequence of a myc and $(His)_6$-tag after the multiple cloning site, which allows to fuse the protein of interest (MuSK-RXC) to the myc and $(His)_6$-tag. The signal peptide of MuSK-R is replaced by the Igκ leader. (FIG. 3). The extracellular domain of MuSK-R without the signal peptide is amplified by PCR using the following primers wherein p means phosphorylated:

| | | |
|---|---|---|
| MuSK 116FPC: | 5' pCT TCC AAA AGC TCC TGT CAT CAC C | SEQ ID NO: 15 |
| MuSK 1532RC: | 5' pCC AGT CAT GGA GTA TGT AGG TGA GAC | SEQ ID NO: 16 |

Primer MuSK116FPC starts with the sequence after the signal peptide (nt 69–93). Primer MuSK1532RC covers the sequence before the transmembrane domain starts and the first 2 amino acids of the transmembrane domain corresponding to nucleotide sequence 1462–1586 of SEQ 1 NO:7. For the PCR reaction ~10 ng hMuSK-R wt DNA are mixed with 1×Pfu buffer, 1 μg of primer MuSK116FPC and 1 μg primer MuSK1532RC, 2.5 μmol of each dNTP, 5 U Pfu polymerase and $H_2O$ in a final volume of 50 μl. The PCR reaction is performed as follows: Cycle 1: 95° C. for 5 min, Cycle 2-i: 96° C. for 0.5 min, 60° C. for 1 min, 72° C. for 6 min, and Cycle 8–27: 95° C. for 0.58 min, 58° C. for 1 min, 72° C. for 6 min; Cycle 28: 72° C. for 10 min. The PCR reaction is cooled to 4° C. in the PCR machine and then gel-purified. The PCR fragment is cloned into to the EcoRV restriction site of pSccTag2b. In this way MuSK-R XC is cloned in frame with the Igk leader at the N-terminus and the myc- and $(His)_6$-tag at the C-terminus. The resulting plasmid is called pSecTag-hMuSK-R.

To express the MuSK-R XC the plasmid pSecTag-hMuSK-R is transfected into 293T cells by the $CaCl_2$ technique (as described in section C). 24 hrs after the transfection, the media is replaced with either fresh DMEM/10% FBS or serum-free X-Vivo 15. Supernatants of the transfected cells are collected after 48 and 72 hrs. A total of 400 ml supernatants are collected and are frozen at −80° C. until the supernatants are purified.

The MuSK-R XC is purified from tissue culture supernatants by immobilized metal affinity chromatography. The metal ion is 0.1 M $NiCl_2$. The column is a 1 or 5 ml Pharmacia metal HiTrap chelating sepharose column. The equilibration buffer (Buffer A) consisted of 20 mM $Na_2HPO_4$ pH 7.4, 1M guanidine hydrochloride, 1M NaCl, filtered through 0.2 μM cellulose acetate filter. The elution buffer (Buffer B) is 20 mM $Na_2HPO_4$, pH 7.4, 1 M guanidine hydrochloride, 1M NaCl, 0.5 M imidazole, filtered through 0.2 μM cellulose acetate filter. The Pharrmacia FPLC chromatography system is used to run columns, with FPLC director program software and a Pharmacia P50 pump. The purification is performed at 4° C.

The pump is primed with buffer A before the load is started. Before the column the column is attached, the load is pumped through until the pink color of the tissue culture media is seen at the connection so that the column is not washed with non-equilibration conditions.

The tissue culture supernatants are adjusted to contain 0.85 M NaCl, 1M guanidinium chloride and 40 mM imidazole and the pH is adjusted to 7.4. The column is equilibrated with 8% buffer B. The sample is loaded and the column then washed in above conditions for seven column volumes. MuSK-R is eluted at 30% Buffer B (150 mM imidazole) over eight column volumes. Fractions are collected from start of the run.

Each fraction is tested in a Dot Blot Assay (see below). Selected positive fractions are tested in Western Blot assays and Elisa (see below). Positive fractions are pooled and dialyzed in 10,000 MWCO membrane (Pierce Snakeskin) against PBS. After dialysis, the optical density is determined at $OD_{280}$. The samples are filtered through 0.2 μM filters and then concentrated in Centricon Centriprep 30 devices in a refrigerated Sorvall RT6000D according to manufacturer's protocol.

To test for positive samples in the dot blot assay, 10 μl of each fraction is pipetted on nitrocellulose. The membrane is dried, blocked with superblock and then probed for MuSK-R protein and developed as described for the India Western (see below).

Western Blots are performed by methods well known in the art. The materials (sample buffer, running buffer and gels) are obtained from Novex.

For western blot analysis 25 to 35 μl/fraction are used. Guanidine containing fractions are precipitated in ice-cold ethanol and are stored on ice for 15 minutes or overnight at 4° C. The samples are centrifuged in refrigerated microcentrifuge (TOMY) at 14,000 rpm for 10 min. The supernatant is discarded, ice-cold acetone is added and centrifuged as before. The pellet is resuspended in SDS sample buffer (Novex) with 5% P-mercaptoethanol in a final volume of 50–70 μl. The samples are denatured at >90° C. for 5 minutes, briefly centrifuged, and 25–35 μl loaded on a 4–20% gradient gel. The gel is blotted onto 0.45 μM nitrocellulose for 1.4 hours at 100 volts, using the Biorad wet transfer blotting cassette with tris-glycine-methanol transfer buffer (25 mM trizma Base, 192 mM glycine, 20% methanol). After blotting the gel, the blot is blocked in Pierce TBS superblock for 10 minutes with mild agitation. The blot is washed twice in TBST (50 mM Tris, pH 7.5, 150 mM NaCl, 0.05% Tween 20) for five min per wash on a rotating platform. The Pierce India™ His-HRP Probe is diluted to 1:5000 in TBST and the blot is incubated with the probe for 1 hour at room temperature and washed 3 times in TBST. After that, horseradish peroxidase reagent (Sigma Fast HRP Insoluble Substrate D4418) is added to the blot and the blot is developed. The blot is washed in three changes of water to stop development. Alternatively an mouse anti-c-myc antibody, (Santa Cruz Biotechnology; CA) is used to detect recombinant MuSK-R protein. This antibody is diluted in superblock to 1 μg/ml final concentration. The blot is washed three times with TBST and then a goat anti-mouse IgG-HRP antibody (Sigma) is added at 1:5000 dilution in superblock. The blot is incubated for I hour at room temperature, with gentle agitation and developed as described above with Fast HRP insoluble substrate (Sigma). The recognized protein traveled at about 85 kD on the SDS PAGE, and it is considered to be 19 kD heavier due to glycosylation.

The recombinant MuSK-R protein is injected into 3 different Balb/c mice. For this purpose 25–50 μg are mixed with 2.25 mg alhydrogel and 100 μg MDP (muranyl dipeptide; Pierce) in a final volume of 200 μl and injected 5 times every 14 days subcutaneously. After the $3^{RD}$ and the $5^{TH}$ injection serum of the 3 mice are tested for reactivity against MuSK-R by FACS analysis and Elisa For FACS analysis the $5\times10^5$ cells of cell lines CEMSS and CEMSS MuSK-R are used. Both the presera and sera are diluted 1:100. 1:300, 1:900 and 1:2700. A rat anti-mouse IgG-PE antibody is used as a secondary reagent at a 1:20 dilution. For the Elisa, 96 well plates are coated with 50 μl of 10 μg/ml anti-mouse $IgGF_c$ (Jackson; Me.) The plates are incubated with various dilutions of sera (1:100 to 1:218700), subsequently with MuSK-R protein and with Nickel activated horse radish peroxidase at a 1:1000 dilution (HRP, Pierce). Nickel activated HRP is binding to the recombinant MuSK-R protein via the $(His)_6$ tag. To develop the Elisa, the plate is incubated with TMP peroxidase substrate (Zymed; CA). In both assays one mouse shows the highest reactivity against native and recombinant MuSK-R. This mouse is boosted with a $6^{th}$ injection of 200 μg MuSK-R protein in PBS. The injection is done subcutaneously and intravenously. 1 week later the spleen is removed, lymphocytes isolated with lympholite M (Accurate Chemicals) and fused, using 50% polyethylene glycol to the myeloma cell line P3X63AG8.0653 using standard procedures. The resulting hybridomas are grown in bulk in HAT media for one week. Viable cells are recovered using lympholite M and cultured in HAT media plus cloning factor (Igen). After the hybridoma are grown for another week, a batch of the cells are cryopreserved in HAT media plus 10% DMSO. Another batch of the cells is subdivided into individual clones by FACSsorting using the single cell deposit unit. The cells are sorted by forward and side scatter and for PI negative cells. The cells are grown up in HT media for two weeks. The supernatants are tested by Elisa and FACS (as described above) for monoclonal antibodies that can recognize native and recombinant MuSK-R protein. The antibodies are isotyped in an Elisa assay by using secondary antibodies that react with IgG1, 2a, 2b, 3, IgM, κ, and λ (Caltag, CA).

Three monoclonal antibodies are identified H1, H2 and H4. All three can react with MuSK-R expressed on the cell ine CEMSS-MuSK-R in a FACS assay. H1 is an IgG1, κ; H2 is IgG1, κ; H4 is IgM antibody.

What is claimed is:

1. A method for identifying transduced mammalian hematopoietic cells comprising:
   a) retrovirally transducing mammalian hematopoietic cells with a nucleic acid sequence encoding a mutated epidermal growth factor receptor (EGFR) operatively linked to an expression control sequence, wherein said mutated EGFR comprises modifications to the intracellular and the extracellular domains, comprises a modification to the extracellular domain, or comprises a modification to the intracellular domain;
   b) incubating the transduced mammalian hematopoietic cells with a marked antibody which recognizes and binds specifically to the mutated EGFR; and
   c) identifying the marked transduced mammalian hematopoietic cells.

2. The method according to claim 1, wherein the mammalian hematopoietic cells are transduced by a retroviral vector selected from the group consisting of a moloney murine leukemia viral vector, a myeloproliferative sacroma viral vector, a murine embryonic stem cell viral vector, a murine stem cell viral vector, and a spleen focus forming viral vector.

3. The method according to claim 1, wherein the mammalian hematopoietic cells are transduced by a lentiviral vector.

4. The method according to claim 1, further comprising the step of separating the identified marked transduced mammalian hematopoietic cells from non-marked mammalian hematopoietic cells.

5. The method according to claim 1, further comprising the step of expanding the marked transduced mammalian hematopoietic cells.

6. The method according to claim 1, wherein the mutated EGFR is a mutated EGFR1.

7. The method according to claim 6, wherein the mutated EGFR1 comprises the amino acid sequence set forth in SEQ ID NO:2 except that amino acid residues 679–1210 are deleted.

8. The method according to claim 6, wherein the mutated EGFR1 comprises the amino acid sequence set forth in SEQ ID NO:2 except that amino acid residues 25–312 and 679–1210 are deleted.

9. A method of identifying mammalian hematopoietic cells expressing a protein of interest, comprising:
   a) introducing into a mammalian hematopoietic cell a nucleic acid comprising a DNA sequence encoding a protein of interest and comprising a DNA sequence encoding a mutated epidermal growth factor receptor 1 (EGFR1), wherein said DNA sequences are operatively linked to one or more expression control sequences, and wherein said mutated EGFR1 comprises modifications to the intracellular and the extracellular domains, comprises a modification to the extracellular domain, or comprises a modification to the intracellular domain;
   b) culturing the resulting mammalian hematopoietic cells; and
   c) identifying mammalian hematopoietic cells which express the mutated EGFR1 thereby obtaining mammalian hematopoietic cells which express the protein of interest.

10. The method according to claim 9, wherein the nucleic acid is introduced by a retroviral vector.

11. The method according to claim 9, wherein the mutated EGFR1 comprises the amino acid sequence set forth in SEQ ID NO:2 except that amino acid residues 679–1210 are deleted.

12. The method according to claim 9, wherein the mutated EGFR1 comprises the amino acid sequence set forth in SEQ ID NO:2 except that amino acid residues 25–312 and 679–1210 are deleted.

13. A method of identifying a genetically modified mammalian cell, comprising:
   a) introducing a nucleic acid sequence encoding a mutated epidermal growth factor receptor 1 (EGFR1), operatively linked to an expression control sequence, into a mammalian cell to form a genetically modified mammalian cell, wherein the mutated EGFR1 either comprises: i) the amino acid sequence set forth in SEQ ID NO:2 except that amino acid residues 679–1210 are deleted, or ii) the amino acid sequence set forth in SEQ ID NO:2 except that amino acid residues 25–312 and 679–1210 are deleted;
   b) allowing expression of the mutated EGFR1 in the genetically modified mammalian cell; and
   c) identifying said genetically modified mammalian cell expressing the mutated EGFR1.

14. The method according to claim 13, wherein the introducing step is accomplished by incorporating the nucleic acid sequence encoding the mutated EGFR1 into a vector and introducing said vector into said mammalian cell.

15. The method according to claim 14, wherein the vector is a retroviral vector.

16. The method according to claim 14, wherein a heterologous coding sequence is also incorporated into said vector.

17. The method according to claim 13, further comprising separating the identified cell expressing the mutated EGFR1.

18. The method according to claim 13, wherein the mammalian cell is a human cell.

19. The method according to claim 18, wherein the human cell is selected from the group consisting of a hematopoietic cell, a liver cell, an endothelial cell and a smooth muscle cell.

20. The method according to claim 18, wherein the human cell is a hematopoietic cell.

21. The method according to claim 20, wherein the hematopoietic cell is a stem cell or T-cell.

22. The method according to claim 13, wherein the identifying step is accomplished by contacting the genetically modified mammalian cell with an antibody that recognizes and binds to the mutated EGFR1.

23. A method of identifying a genetically modified cell, comprising:
   a) introducing into a cell a nucleic acid sequence encoding a mutated epidermal growth factor receptor (EGFR), operatively linked to an expression control sequence, to form a genetically modified cell, wherein said cell is a human hematopoietic cell, a human liver cell, a human endothelial cell, or a human smooth muscle cell, and wherein said mutated EGFR comprises modifications to the intracellular and 1be extracellular domains, comprises a modification to the extracellular domain, or comprises a modification to the intracellular domain;
   b) allowing expression of the mutated EGFR in the genetically modified cell; and
   c) identifying said genetically modified cell expressing the mutated EGFR.

24. The method according to claim 23, wherein the cell is a human hematopoietic cell.

25. The method according to claim 24, wherein the human hematopoietic cell is a stem cell or T-cell.

26. The method according to claim 23, wherein the mutated EGFR is a mutated EGFR1.

27. The method according to claim 26, wherein the mutated EGFR1 comprises the amino acid sequence set forth in SEQ ID NO:2 except that amino acid residues 679–1210 are deleted.

28. The method according to claim 26, wherein the mutated EGFR1 comprises the amino acid sequence set forth in SEQ ID NO:2 except that amino acid residues 25–312 and 679–1210 are deleted.

29. The method according to claim 23, wherein the introducing step is accomplished by incorporating the nucleic acid sequence encoding the mutated EGFR into a vector and introducing said vector into said call.

30. The method according to claim 29, wherein the vector is a retroviral vector.

31. The method according to claim 29, wherein a heterologous coding sequence is also incorporated into said vector.

32. The method according to claim 23, further comprising separating the identified cell expressing the mutated EGFR.

33. The method according to claim 23, wherein the identifying step is accomplished by contacting the genetically modified cell with an antibody that recognizes and binds to the mutated EGFR.

34. A method for identifying transduced mammalian cells comprising:
   a) transducing mammalian cells with a lentiviral vector comprising a nucleic acid sequence encoding a mutated epidermal growth factor receptor (EGFR) operatively linked to an expression control sequence, wherein said mutated EGFR comprises modifications to the intracellular and the extracellular domains, comprises a modification to the extracellular domain, or comprises a modification to the intracellular domain;

b) incubating the transduced mammalian cells with a marked antibody which recognizes and binds specifically to the mutated EGFR; and c) identifying the marked transduced mammalian cells.

35. The method according to claim 34, wherein the mutated EGFR is a mutated EGFR1.

36. The method according to claim 35, wherein the mutated EGFR1 comprises the amino acid sequence set forth in SEQ ID NO:2 except that amino acid residues 679–1210 are deleted.

37. The method according to claim 35, wherein the mutated EGFR1 comprises the amino acid sequence set forth in SEQ ID NO:2 except that amino acid residues 25–312 and 679–1210 are deleted.

38. The method according to claim 34, wherein the mammalian cells are human cells.

39. The method according to claim 38, wherein the human cells are selected from the group consisting of hematopoietic cells, liver cells, endothelial cells and smooth muscle cells.

40. The method according to claim 38, wherein the human cells are hematopoietic cells.

41. The method according to claim 40, wherein the hematopoietic cells are stem cells or T-cells.

42. The method according to claim 34, wherein said lentiviral vector also comprises a nucleic acid sequence encoding a heterologous protein of interest.

43. The method according to claim 34, wherein the identifying step is accomplished by contacting the genetically modified mammalian cell with an antibody that recognizes and binds to the mutated EGFR.

* * * * *